(12) United States Patent
Meridew et al.

(10) Patent No.: US 9,744,047 B2
(45) Date of Patent: Aug. 29, 2017

(54) IMPLANT FIXATION DEVICE

(71) Applicant: Biomet Manufacturing, LLC, Warsaw, IN (US)

(72) Inventors: Jason D. Meridew, Warsaw, IN (US); John R. White, Winona Lake, IN (US); Mark A. Bollinger, Fort Wayne, IN (US); W. Jason Slone, Silver Lake, IN (US); Kirk J. Bailey, Rochester, IN (US); Jon C. Serbousek, Winona Lake, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 14/635,056

(22) Filed: Mar. 2, 2015

(65) Prior Publication Data
US 2015/0238319 A1 Aug. 27, 2015

Related U.S. Application Data

(62) Division of application No. 13/761,345, filed on Feb. 7, 2013, now Pat. No. 8,968,415.

(60) Provisional application No. 61/595,832, filed on Feb. 7, 2012.

(51) Int. Cl.
*A61F 2/34* (2006.01)
*A61F 2/36* (2006.01)
*A61F 2/30* (2006.01)
*A61F 2/46* (2006.01)
*A61F 2/32* (2006.01)

(52) U.S. Cl.
CPC .......... *A61F 2/367* (2013.01); *A61F 2/30734* (2013.01); *A61F 2/30749* (2013.01); *A61F 2/34* (2013.01); *A61F 2/3601* (2013.01); *A61F 2/4609* (2013.01); *A61F 2002/30332* (2013.01); *A61F 2002/30378* (2013.01); *A61F 2002/30507* (2013.01); *A61F 2002/30565* (2013.01); *A61F 2002/30579* (2013.01); *A61F 2002/30841* (2013.01); *A61F 2002/3241* (2013.01); *A61F 2002/3403* (2013.01); *A61F 2002/3429* (2013.01); *A61F 2002/3631* (2013.01); *A61F 2002/3668* (2013.01); *A61F 2002/4629* (2013.01)

(58) Field of Classification Search
CPC ...... A61F 2/34; A61F 2/36; A61F 2002/3429; A61F 2220/0033; A61F 2/367
See application file for complete search history.

(56) References Cited

U.S. PATENT DOCUMENTS

| 6,319,255 B1 * | 11/2001 | Grundei | A61B 17/70 606/246 |
| 8,308,810 B2 | 11/2012 | Meridew | |

* cited by examiner

*Primary Examiner* — Jason-Dennis Stewart
(74) *Attorney, Agent, or Firm* — Schwegman Lundberg & Woessner, P.A.

(57) ABSTRACT

Disclosed is an orthopedic implant that includes an anchor, a bore, and a compressible and expandable mesh. The anchor is configured to secure the implant at an implantation site and defines a longitudinal axis. The bore is defined by the anchor and extends along the longitudinal axis. The compressible and expandable mesh is aligned along the longitudinal axis and defines a plurality of openings. The mesh is configured to compress along the longitudinal axis and expand from the longitudinal axis to engage surrounding bone or tissue at the implantation site to secure the implant at the implantation site.

20 Claims, 26 Drawing Sheets

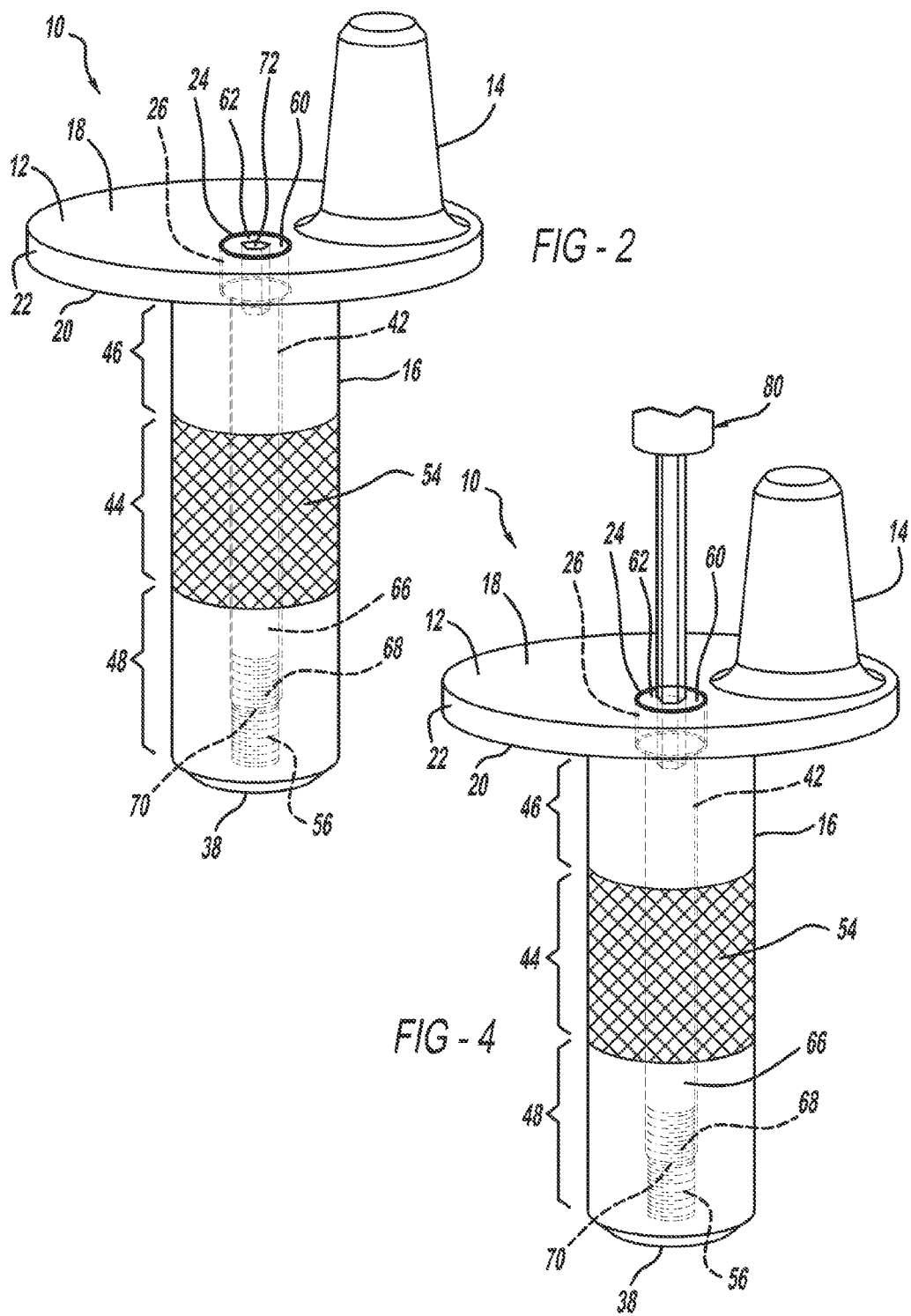

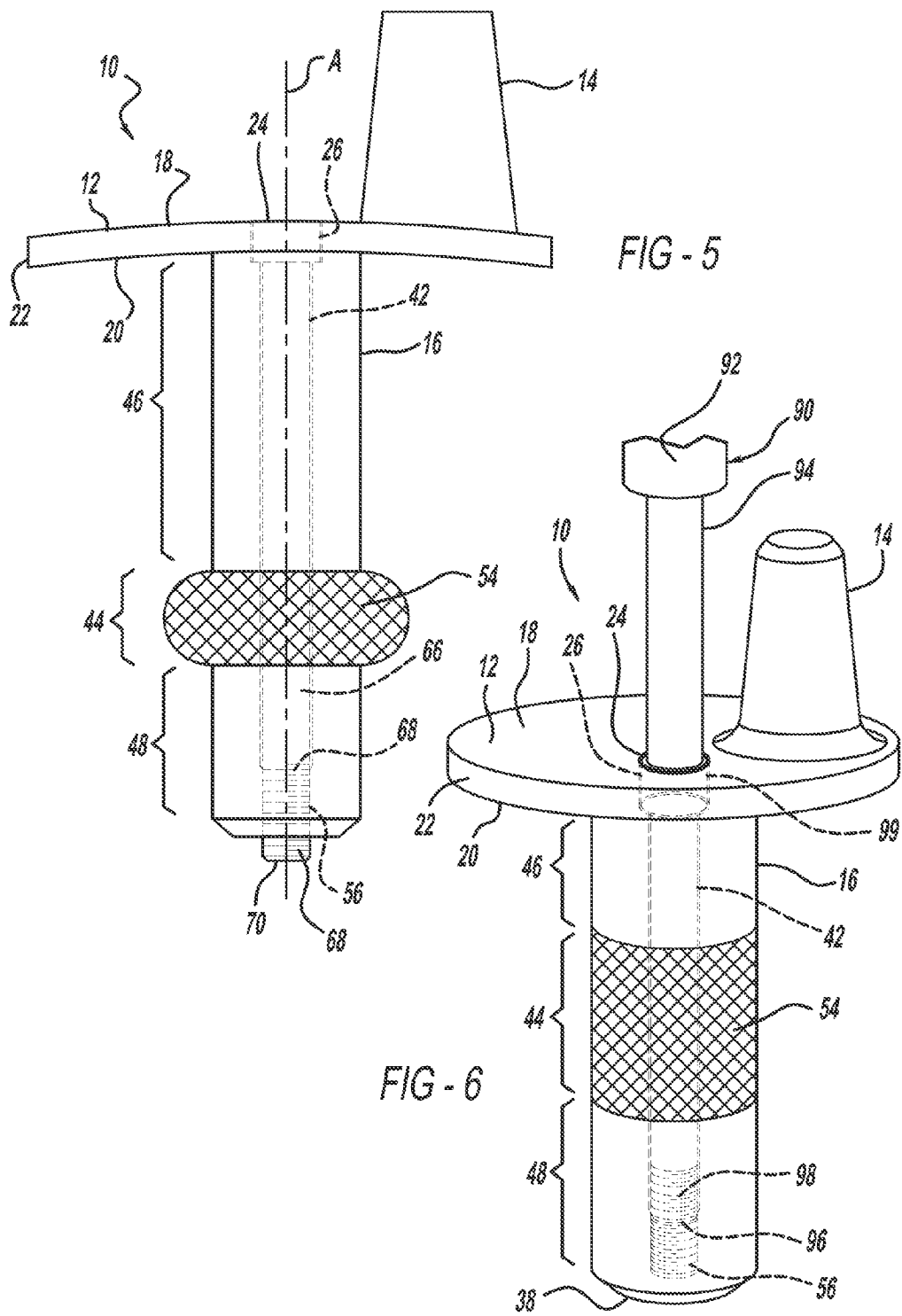

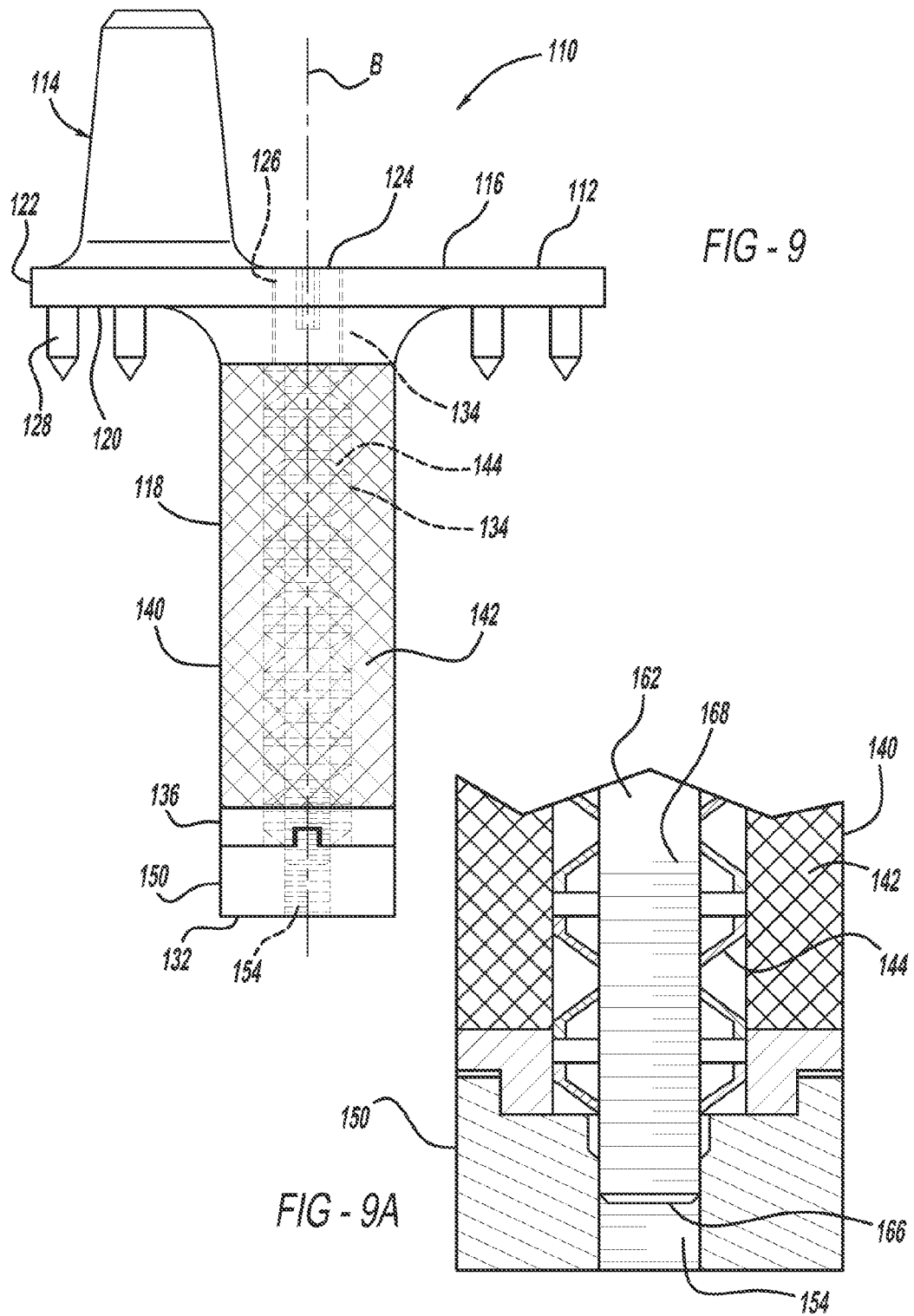

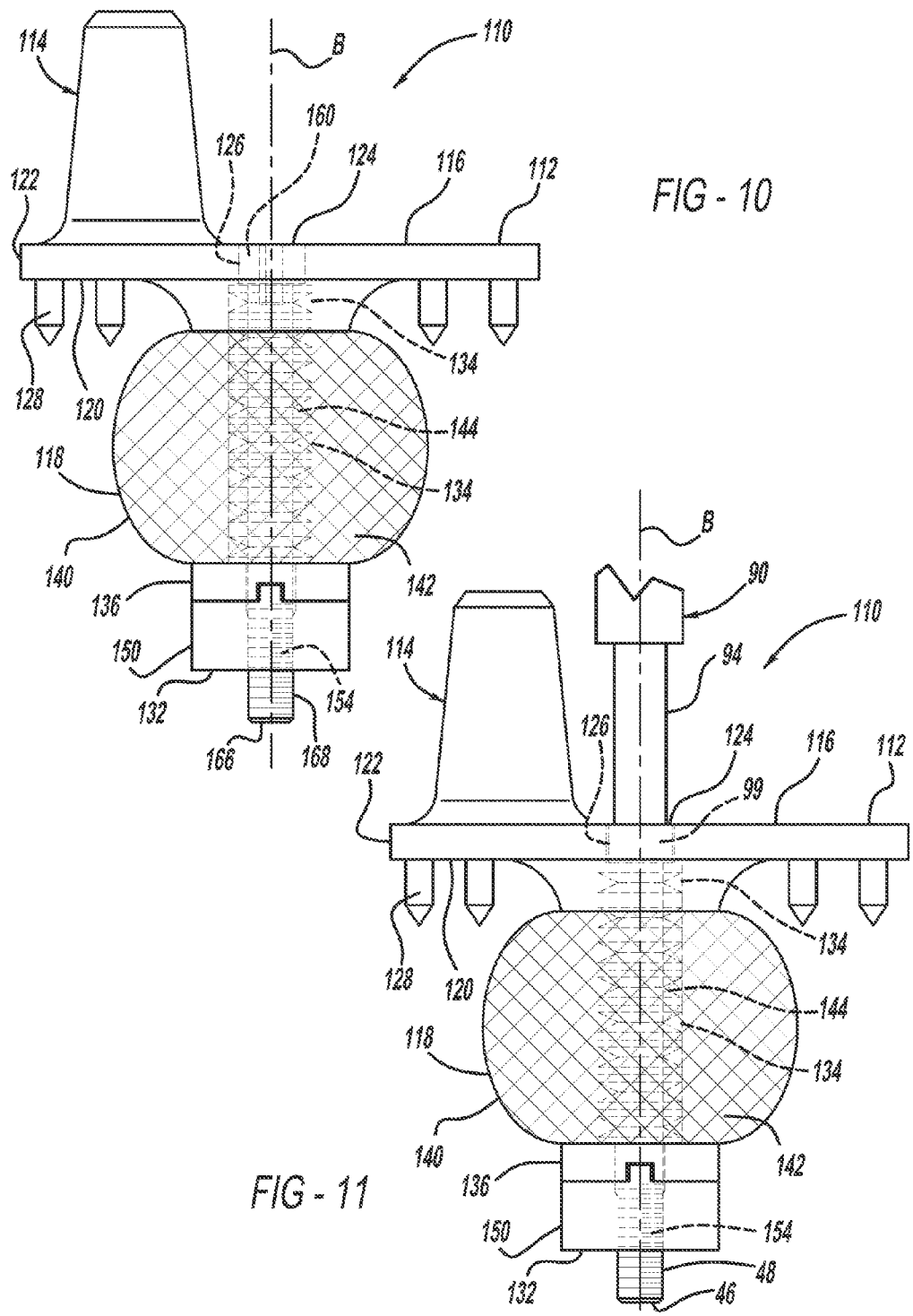

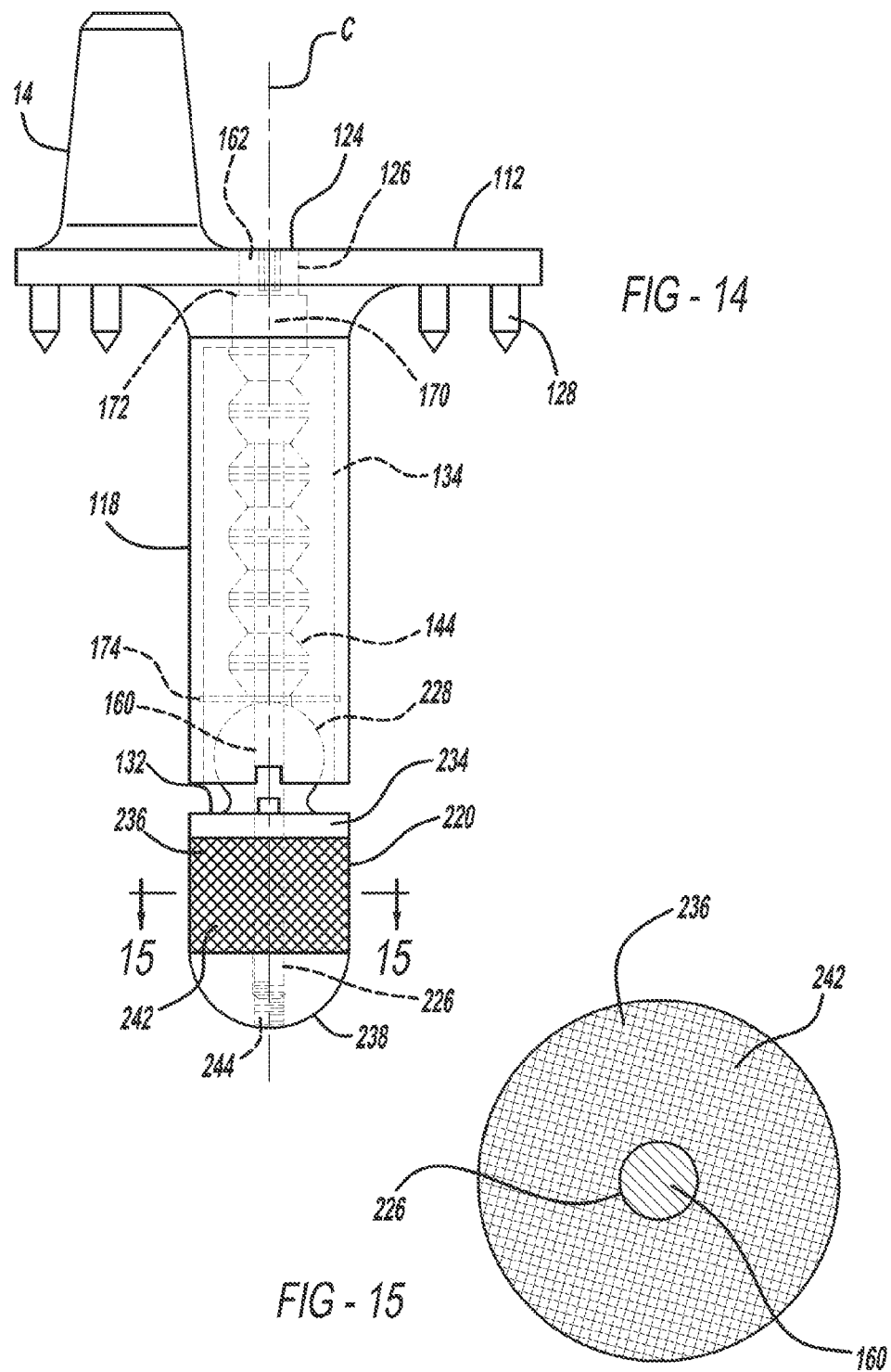

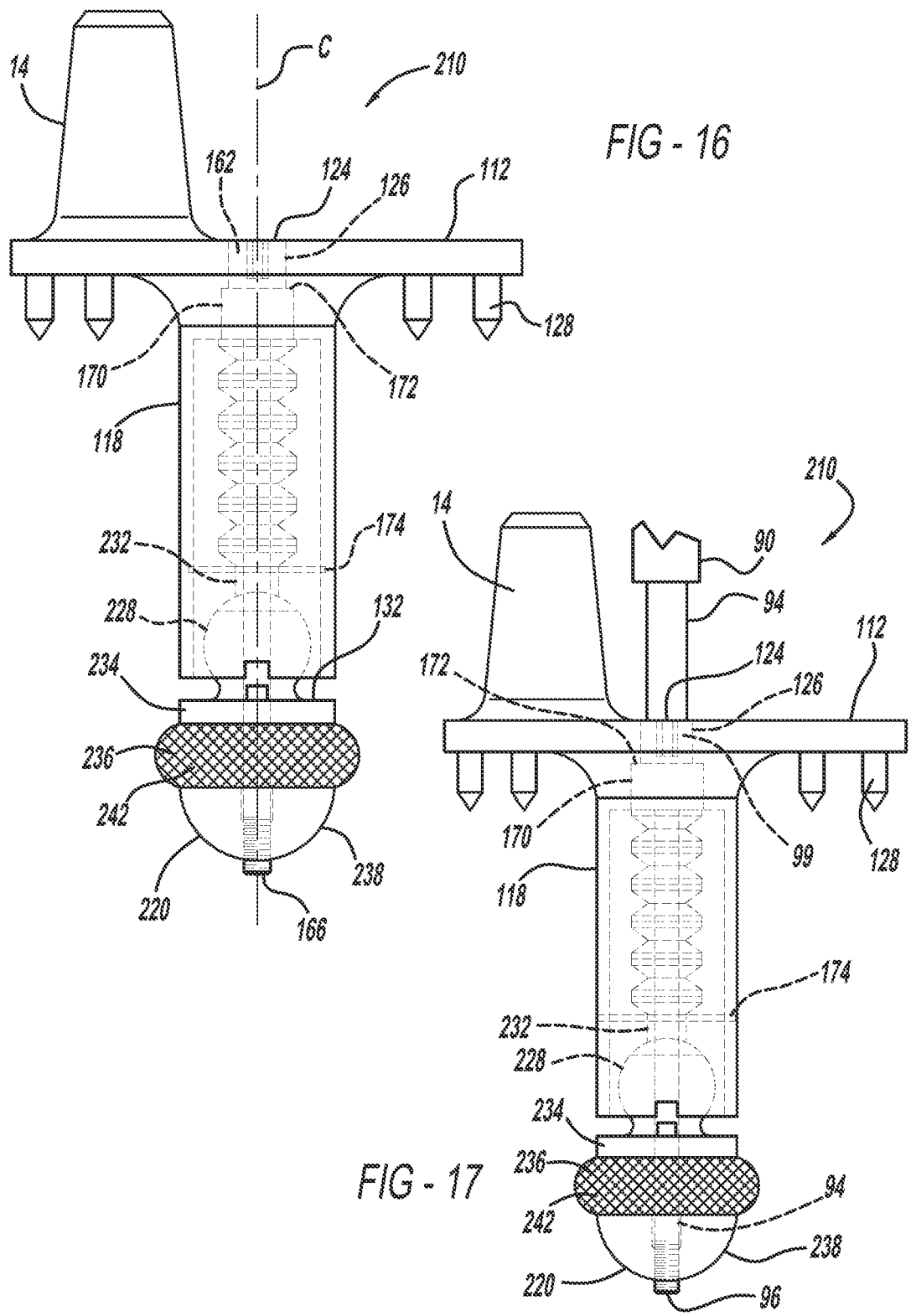

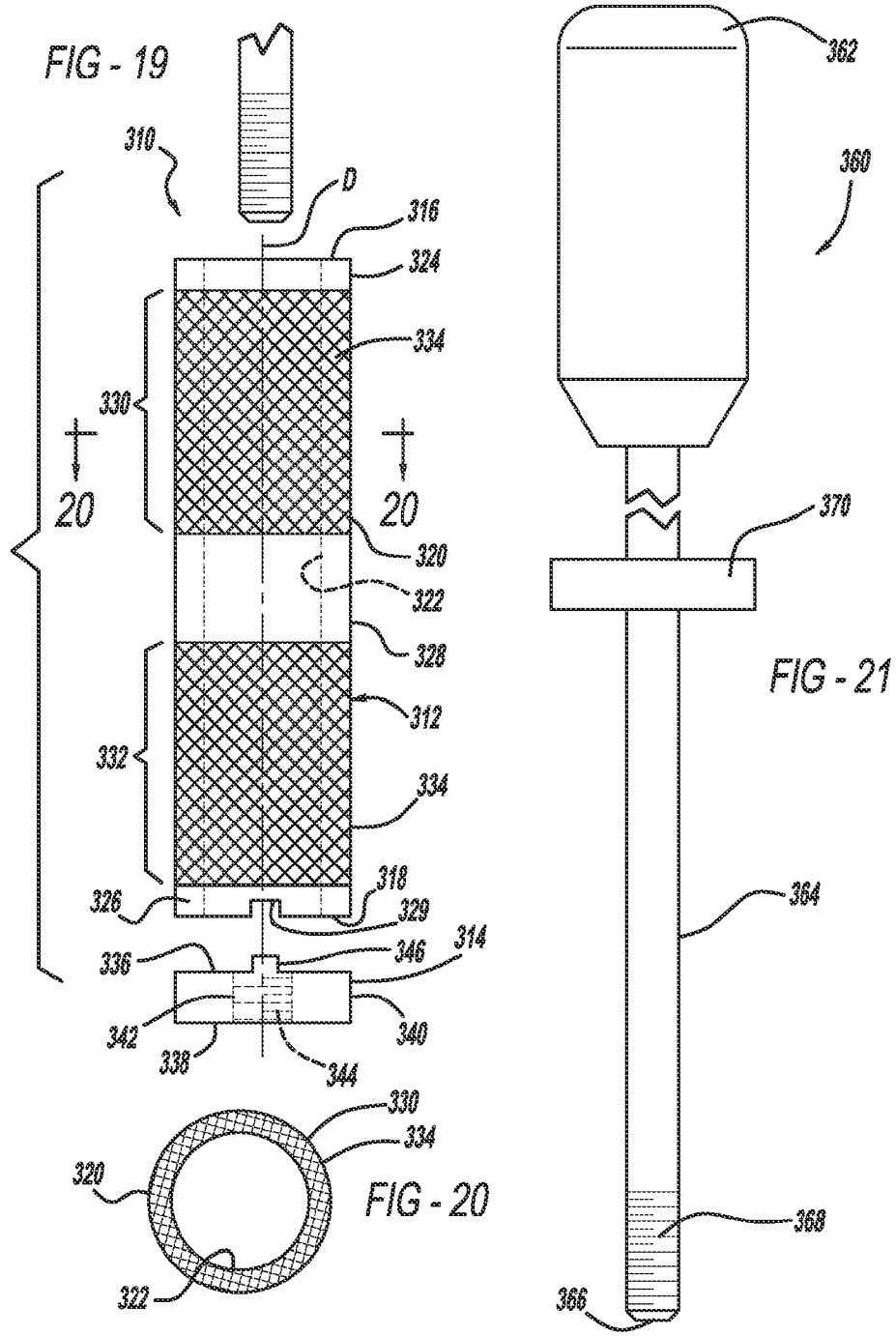

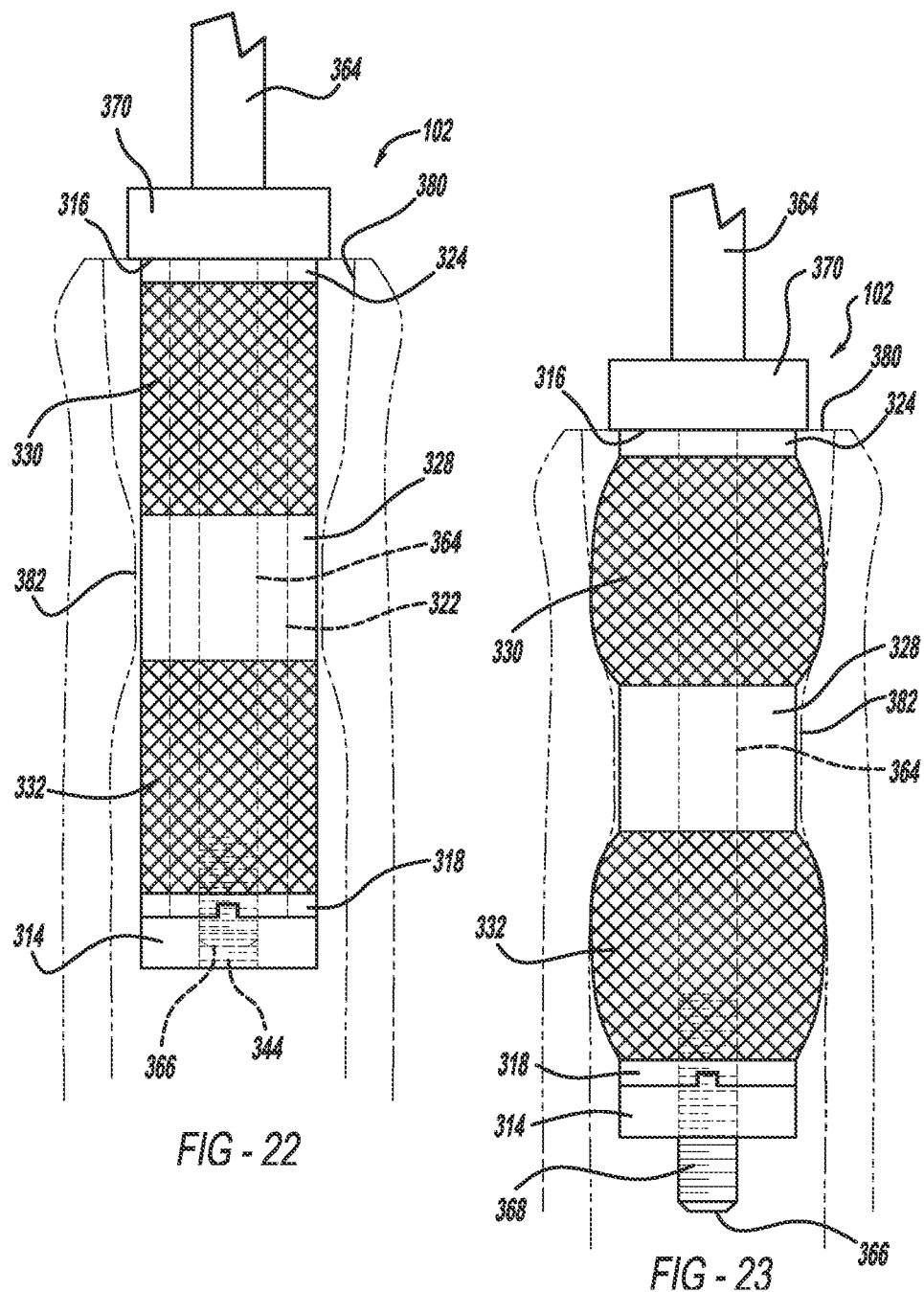

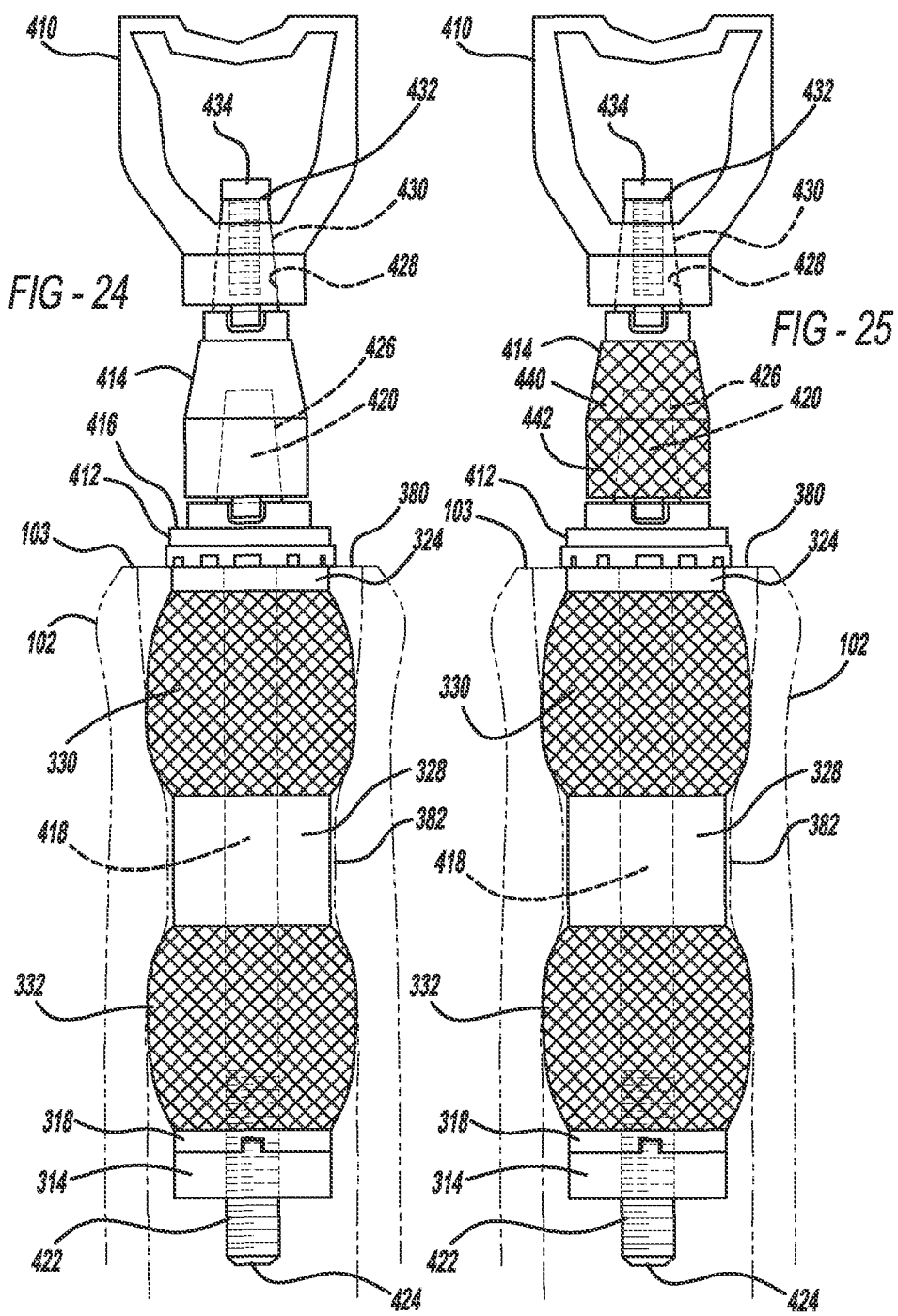

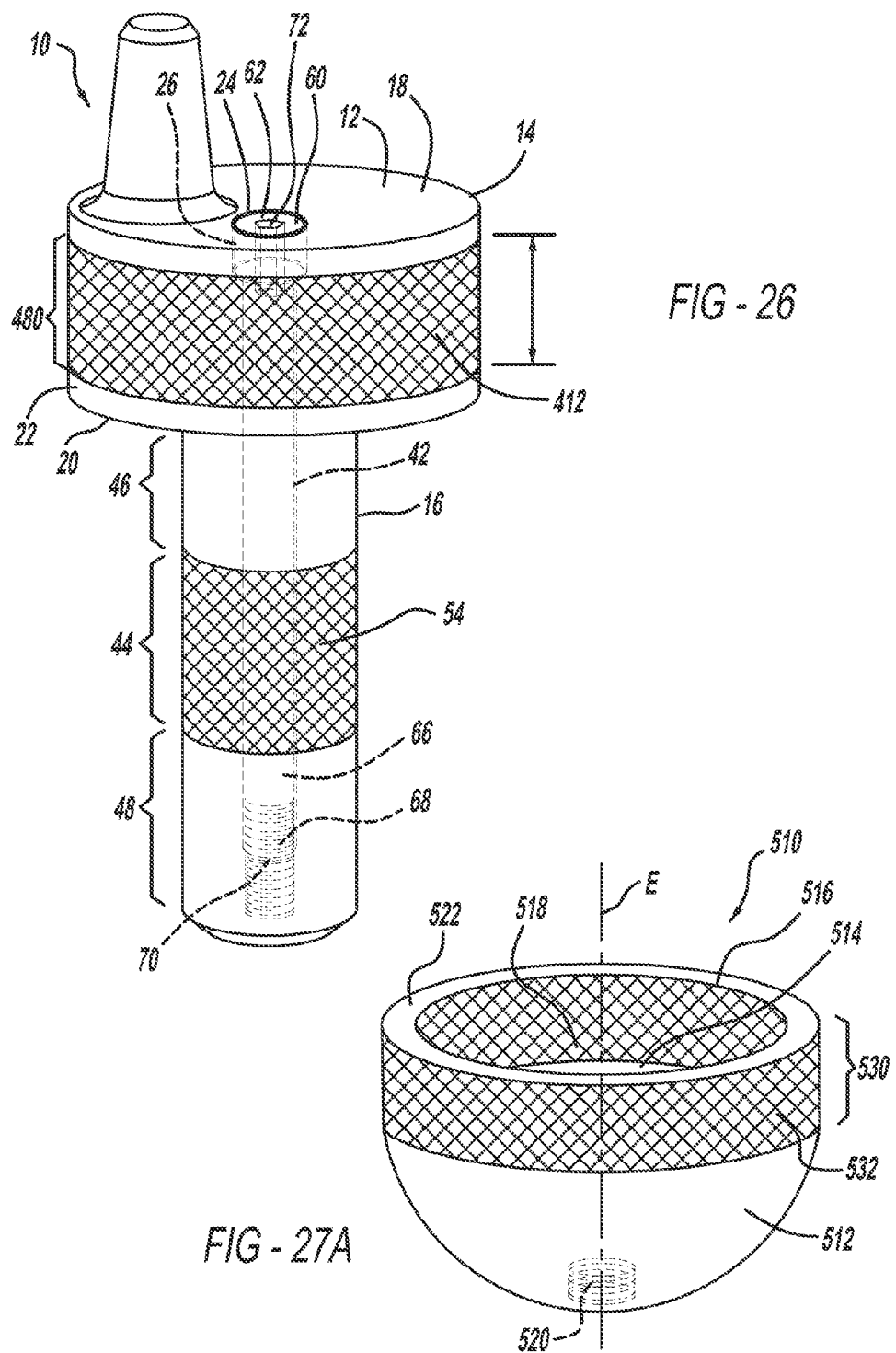

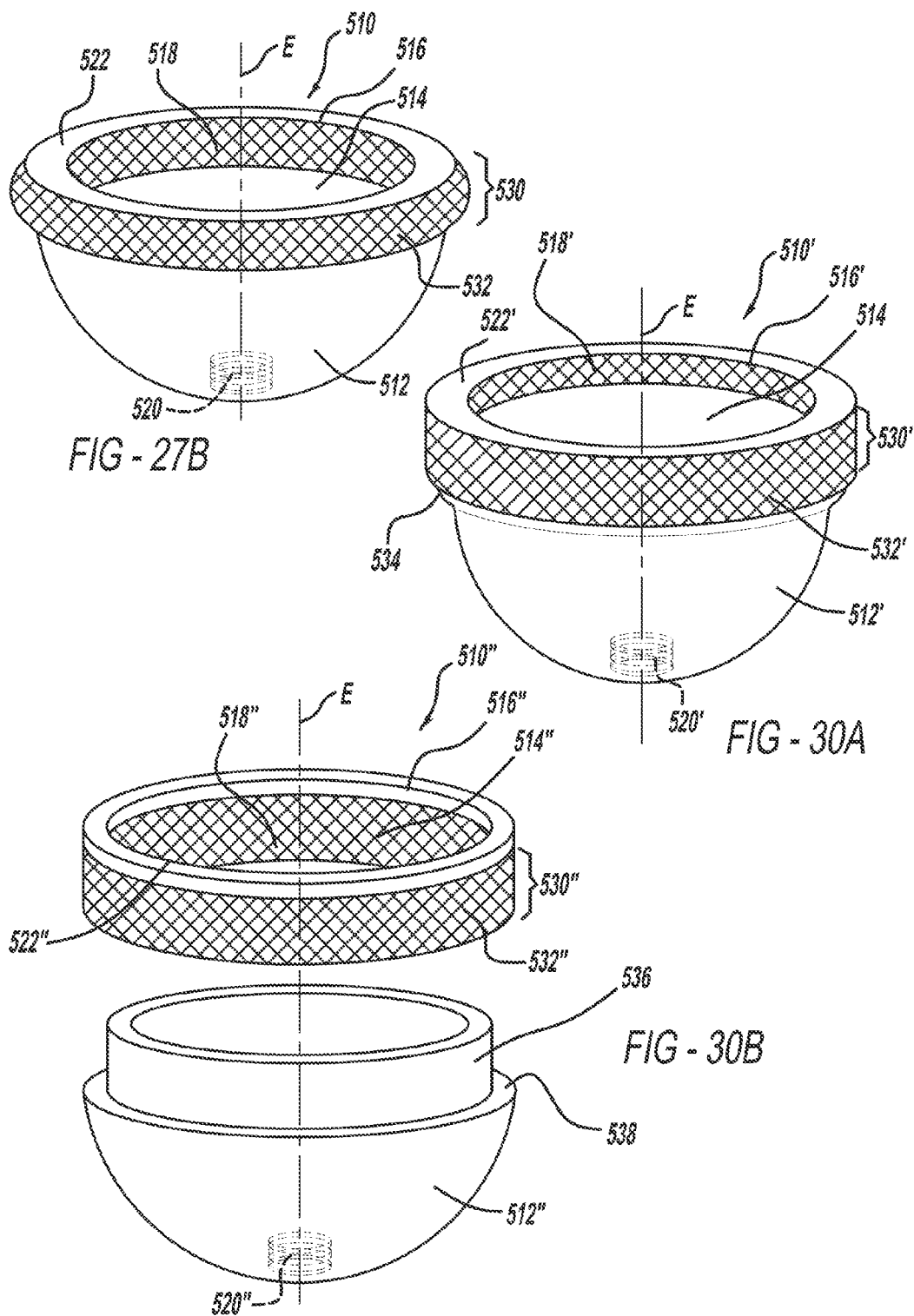

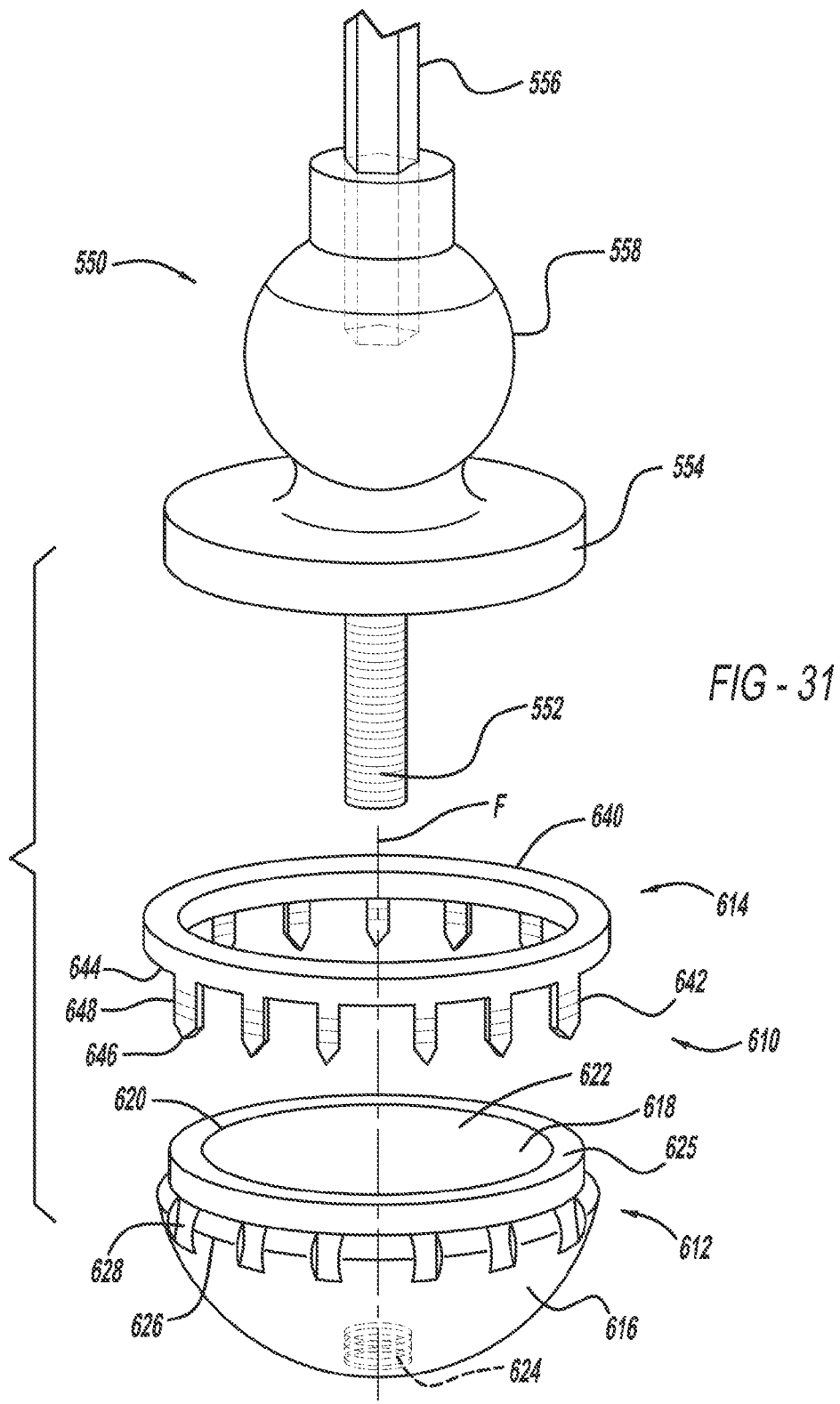

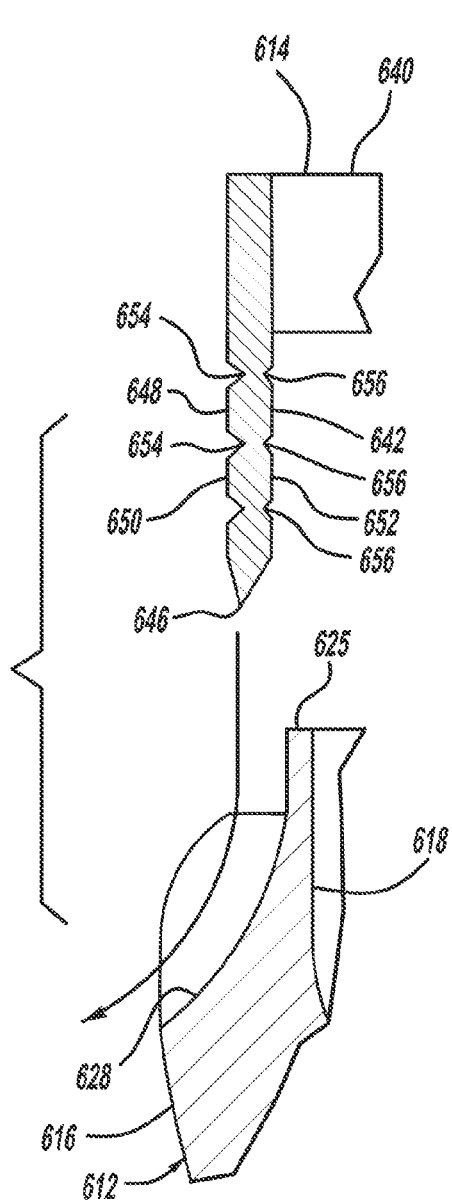
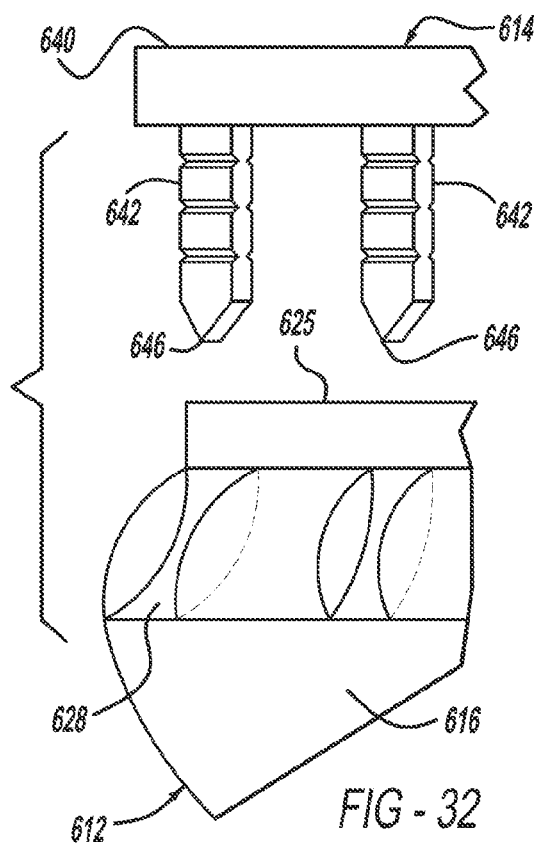
FIG - 32
FIG - 33
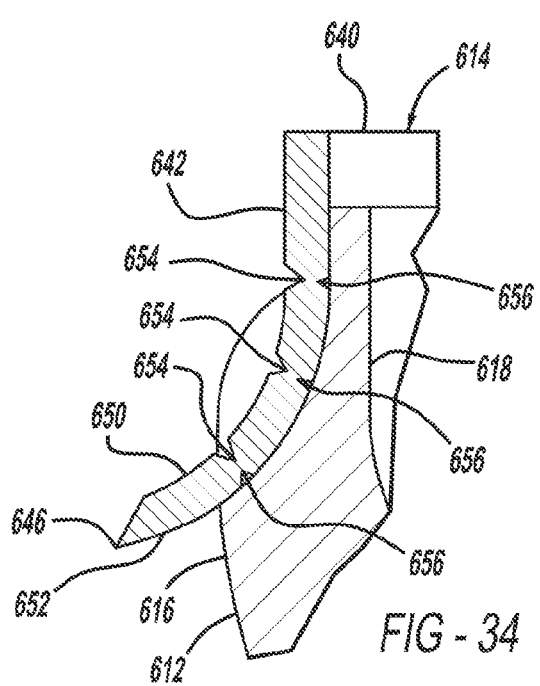
FIG - 34

IMPLANT FIXATION DEVICE

CROSS-REFERENCE TO RELATED APPLICATIONS

This application is a divisional of U.S. patent application Ser. No. 13/761,345 filed on Feb. 7, 2013, now U.S. Pat. No. 8,968,415, which claims the benefit of U.S. Provisional Application No. 61/595,832, filed on Feb. 7, 2012. The entire disclosure of the above application is incorporated herein by reference.

FIELD

The present disclosure relates to orthopedic implant fixation devices, including expandable fixation devices.

BACKGROUND

This section provides background information related to the present disclosure, which is not necessarily prior art.

To secure orthopedic implants to bone, various fixation devices are often used, such as pins and screws. While current fixation devices are suitable for their intended use, they are subject to improvement.

SUMMARY

This section provides a general summary of the disclosure, and is not a comprehensive disclosure of its full scope or all of its features.

The present teachings provide for an orthopedic implant that includes an anchor, a bore, and a compressible and expandable mesh. The anchor is configured to secure the implant at an implantation site and defines a longitudinal axis. The bore is defined by the anchor and extends along the longitudinal axis. The compressible and expandable mesh is aligned along the longitudinal axis and defines a plurality of openings. The mesh is configured to compress along the longitudinal axis and expand from the longitudinal axis to engage surrounding bone or tissue at the implantation site to secure the implant at the implantation site.

The present teachings further provide for an orthopedic implant that includes a hemispherical bone engaging outer surface, a concave articulation surface, and a retention component. The concave articulation surface is opposite to the bone engaging surface. An axis of the implant extends through an axial center of the concave articulation surface. The retention component is at an exterior of the implant and is configured to compress along the axis and expand from the axis to engage surrounding bone or tissue at an implantation site to secure the implant at the implantation site.

The present teachings still further provide for an orthopedic implant including a base, an anchor, a connector, and a resiliently compressible mesh portion. The base includes a first side and a second side that is opposite to the first side. The anchor extends from the first side of the base. The connector extends from the second side of the base. The resiliently compressible mesh component is included in the base portion or attached to the connector. The mesh component is configured to retain the implant at an implantation site.

The present teachings also provide for an orthopedic implant that includes a cup component and a retention component. The cup component includes a hemispherical bone engaging outer surface, a concave articulation surface, and a plurality of concave biasing surfaces. The concave articulation surface is opposite to the bone engaging surface. The axis of the cup component extends through an axial center of the concave articulation surface. The plurality of concave biasing surfaces are spaced apart about an equator of the hemispherical bone engaging surface. The retention component includes a retention ring and a plurality of retention barbs that extend from the retention ring and are spaced apart about the retention ring. Upon compression of the retention component onto the cup component such that the retention barbs contact the biasing surfaces, the retention barbs are forced outward from the axis to engage surrounding bone or tissue at an implantation site to secure the implant at the implantation site.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 2 is a perspective view of the implant of FIG. 1;

FIG. 4 is a perspective view of the implant of FIG. 1 in cooperation with a driver;

FIG. 5 is a side-view of the implant of FIG. 1 in a compressed position;

FIG. 6 is a perspective view of the implant of FIG. 1 in cooperation with a compression tool;

FIG. 9 is a side view of the implant of FIG. 8;

FIG. 9A is a close-up sectional view of interaction between a fastener and a receptacle of the implant of FIG. 9;

FIG. 10 is a side view of the implant of FIG. 9 in a compressed position;

FIG. 11 is a side view of the implant of FIG. 9 moved to a compressed position with a compression tool;

FIG. 14 is a side view of the implant of FIG. 13;

FIG. 15 is a cross-sectional view taken along line 15-15 of FIG. 15;

FIG. 16 is a side view of the implant of FIG. 13 in a compressed position;

FIG. 17 is a side view of the implant of FIG. 13 moved to a compressed position with a compression tool;

FIG. 19 is a disassembled view of another implant according to the present teachings;

FIG. 20 is a cross-sectional view taken along line 20-20 of FIG. 19;

FIG. 21 is a side view of a sleeve compression tool;

FIG. 22 is a side view of the implant of FIG. 19 in an uncompressed position in a femur bone;

FIG. 23 is a side view of the implant of FIG. 19 in a compressed position and anchored in a femur;

FIG. 24 is a side view of the implant of FIG. 19 anchored in a femur with a distal femoral implant secured thereto;

FIG. 25 is a side view of the implant of FIG. 19 anchored in a femur with a distal femoral implant secured thereto, the distal femoral implant including a compressible mesh portion;

FIG. 26 is a perspective view of another implant according to the present teachings;

FIG. 27A is a perspective view of an additional implant according to the present teachings in an uncompressed position, the implant configured as an acetabular cup implant;

FIG. 27B is a perspective view of the implant of FIG. 27A, the implant in a compressed position;

FIG. 30A is a perspective view of another implant according to the present teachings;

FIG. 30B is a perspective view of a further implant of the present teachings;

FIG. 31 is an exploded view of an another implant according to the present teachings;

FIG. 32 is another view of the implant of FIG. 31;

FIG. 33 is a sectional view illustrating assembly of the implant of FIG. 31;

FIG. 34 is a sectional view illustrating the implant of FIG. 31 assembled;

Corresponding reference numerals indicate corresponding parts throughout the several views of the drawings.

DETAILED DESCRIPTION

Figures 1, 1A, 3:
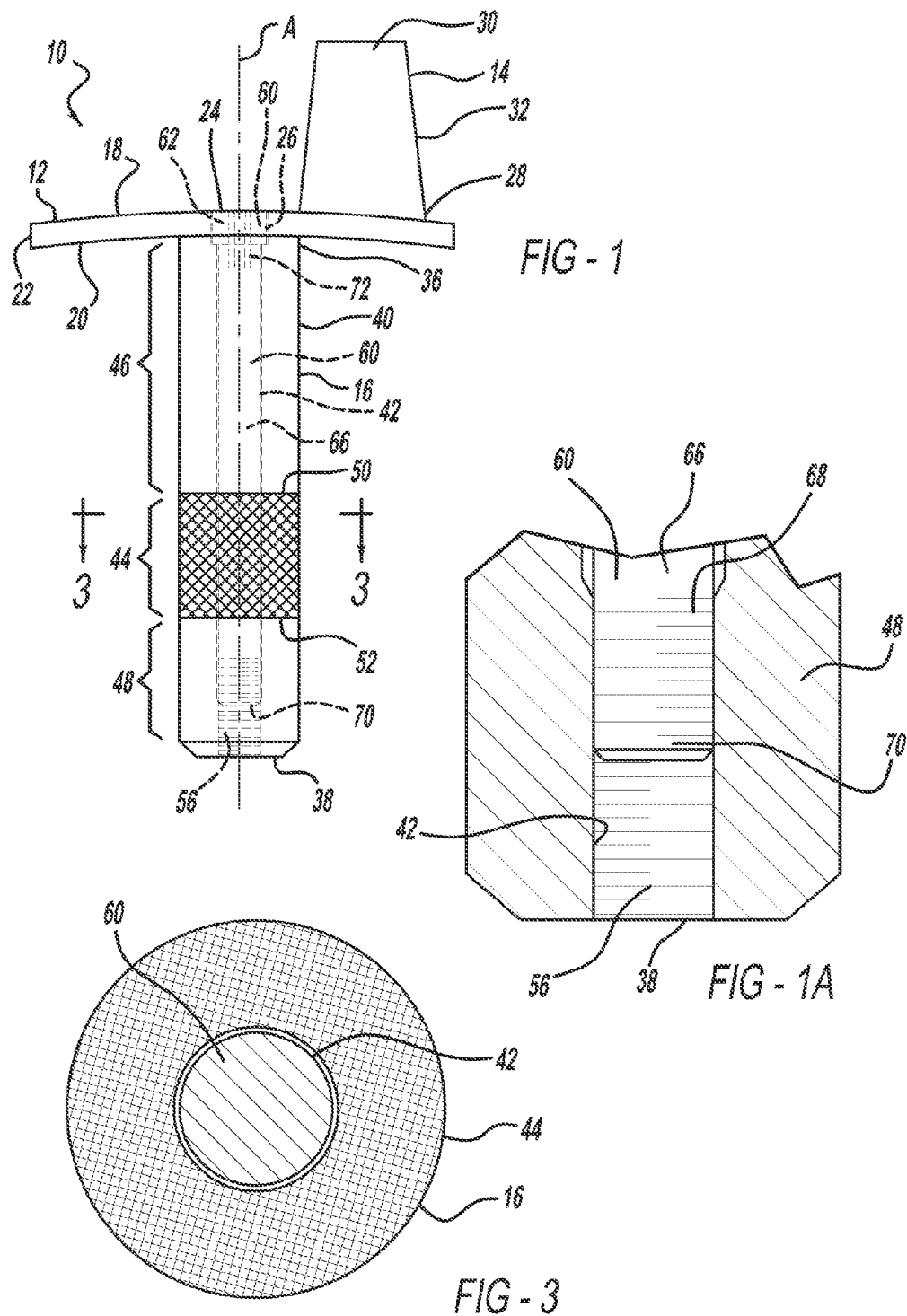
FIG. 1 is a side view of an implant according to the present teachings.
FIG. 1A is a close-up sectional view of interaction between a fastener and a bore of the implant of FIG. 1.
FIG. 3 is a cross-sectional view taken along line 3-3 of FIG. 1.

Example embodiments will now be described more fully with reference to the accompanying drawings.

With initial reference to FIGS. 1-5, an orthopedic implant according to the present teachings is illustrated at reference numeral 10. The implant 10 generally includes a base 12, a connector or coupler 14, and an anchor or stem 16. The base 12 is between the connector 14 and the stem 16.

The base 12 generally includes a first surface 18, a second surface 20 that is opposite to the first surface 18, and a side surface 22 that is between the first surface 18 and the second surface 20. The base 12 defines an aperture 24 at the first surface 18. The aperture 24 is aligned with, and provides access to, a counterbore 26 defined by the base 12. The aperture 24 and the counterbore 26 are generally at an axial center of the base 12, which is aligned with a longitudinal axis A of the stem. As illustrated in FIG. 2 for example, the side surface 22 generally defines an oval shape and the second surface 20 generally defines a concave shape. The base 12 can define any other suitable shape to correspond to an opposing surface that contacts or is near the implant 10 when implanted.

Figure 7:
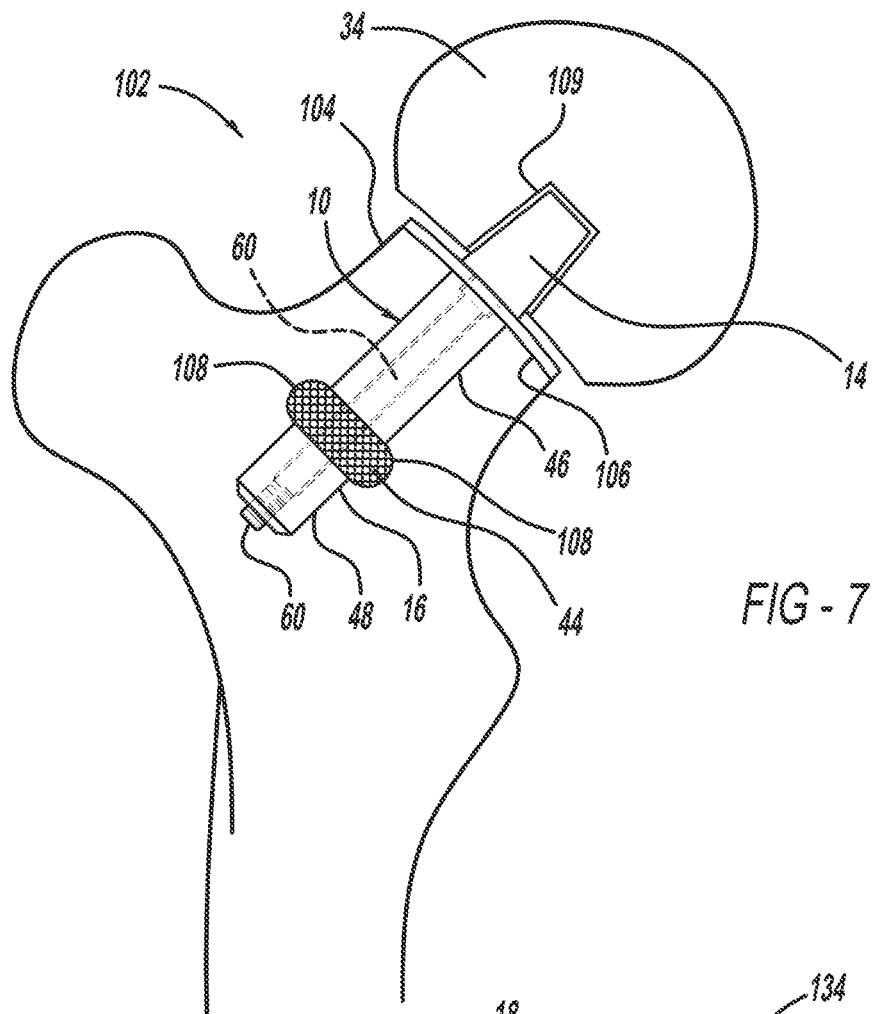
FIG. 7 illustrates the implant of FIG. 1 implanted in a femur bone.

The connector 14 extends from the first surface 18 of the base 12. As illustrated, the connector 14 is offset from the center of the first surface 18 and the longitudinal axis A. The connector 14 includes a base end 28 at the first surface 18 and a tip end 30 that is opposite to the base end 28. A sidewall 32 extends between the base end 28 and the tip end 30. The sidewall 32 is tapered from the base end 28 to the tip end 30 such that the sidewall 32 has a smaller diameter at the tip end 30 than the base end 28, thereby providing the connector 14 with a male Morse taper surface. The connector 14 can be integral with the base 12 or mounted to the base 12 in any suitable manner, such as with a weld. The connector 14 can be any suitable connector for connecting another implant component to the connector 14, such as a femoral head 34 (FIG. 7). The connector 14 may also be aligned with the longitudinal axis A or positioned at any other suitable location of the first surface 18.

The stem 16 generally includes a base end 36 at the second surface 20 of the base 12 and a tip end 38 that is opposite to the base end 36. A cylindrical sidewall 40 extends between the base end 36 and the tip end 38. The base end 36 of the stem 16 can be integral with the base 12 or mounted to the base 12 in any suitable manner, such as with a weld. The stem 16 defines a bore 42 that extends along the longitudinal axis A from the counterbore 26 to the tip end 38. The bore 42 is generally cylindrical, as illustrated in FIG. 3 for example.

The stem 16 further includes a compressible mesh portion 44, which is between a first stem portion 46 and a second stem portion 48. The first stem portion 46 is between the base end 36 and the compressible mesh portion 44. The second stem portion 48 is between the compressible mesh portion 44 and the tip end 38. The first stem portion 46 and the second stem portion 48 are generally non-compressible. As in the illustrated example, the compressible mesh portion 44 extends from a point about half-way between the base end 36 and the tip end 38 to a point about three-quarters between the base end 36 and the tip end 38. However, the mesh portion 44 can be at any suitable position between the base end 36 and the tip end 38 and be of any suitable length.

The compressible mesh portion 44 includes a first end 50 that abuts the first stem portion 46 and a second end 52 that abuts the second stem portion 48. The first end 50 of the mesh portion 44 can be secured to the first stem portion 46 and the second end 52 can be secured to the second stem portion 48 in any suitable manner, such as with a weld. The first stem portion 46, the second stem portion 48, and compressible mesh portion 44 can also be unitary or monolithic, and thus formed from a single metallic portion, as further described herein.

At the compressible mesh portion 44, the sidewall 40 defines a plurality of openings 54. At the first stem portion 46 and the second stem portion 48 the sidewall 40 is generally solid. The openings 54 can be of any suitable shape and size to permit compression of the mesh portion 44 along the longitudinal axis A and expansion of the mesh portion 44 away from the longitudinal axis A in a direction generally perpendicular to the longitudinal axis A (as further described herein and illustrated in FIG. 5). For example, the openings 54 can be in the form of a lattice structure with generally uniform and adjacent diamond-shaped openings of any suitable size, such as from about 0.25 mm to about 5.0 mm, such as about 1.0 mm. The openings 54 can also be generally spaced apart slots extending generally parallel to the longitudinal axis A and spaced apart at any suitable distance, such as from about 0.10 mm to about 1.0 mm, such as about 0.5 mm, and can be of any suitable size, such as from about 0.25 mm to about 5.0 mm, such as about 1.0 mm or about 2.0 mm.

The mesh portion 44 can also define openings 54 of any other suitable size and shape, such as circular, hexagonal, octagonal, parallelogram, or rhombus shaped openings. The shape can be selected depending on the degree of retention force or grip desired between the mesh portion 44 and, for example, surrounding bone. For example, upon compression of the mesh portion 44, diamond shaped openings will have sharper edges to more securely engage surrounding bone as compared to, for example, circular openings. Hexagonal and octagonal shaped openings will often provide greater retention force when compressed to engage bone than circular openings, but less than diamond shaped openings.

The openings 54 defined by the mesh portion 44 can be formed in any suitable manner using any suitable manufacturing device and/or technique, such as wire electrical discharge machining, laser cutting, furnace brazing, fusion bonding, EOS laser sintering, and rapid metal prototyping. For example, the openings 54 can be formed using wire electrical discharge machining to cut completely through a wall of the stem 16 to define the openings 54 therein. Further or alternatively, lattice material defining the openings 54 can be connected, such as by welding, between the first stem portion 46 and the second stem portion 48. The compressible mesh portion 44 can include any suitable material, such as a suitable biocompatible metal or polymer.

At the second stem portion 48, the bore 42 includes a plurality of internal threads 56. The threads 56 can extend from the tip end 38 to nearly the compressible mesh portion 44.

A fastener 60 is seated in the bore 42. The fastener 60 includes a head 62 and a shaft 66, which includes external fastener threads 68 at a distal end 70. In the uncompressed position of FIGS. 1, 1A, 2, and 4, the shaft 66 is positioned such that the anchor head 62 is seated within the counterbore 26, the shaft 66 extends through a majority of the stem 16, and the first few fastener threads 68 at the distal end 70 engage the threads 56 of the bore 42 that are closest to the mesh portion 44. The head 62 includes a coupler 72 configured to mate with a suitable device for rotating the fastener 60, such as a driver 80.

As illustrated in FIGS. 4 and 5 for example, the compressible mesh portion 44 can be compressed by rotating the fastener 60 with the driver 80. Rotation of the fastener 60 causes the fastener 60 to cooperate with additional threads 56 of the bore 42. Because the fastener 60 is restricted from moving along the longitudinal axis A due to cooperation between the head 62 and the counterbore 26, the tip end 38 and the second stem portion 48 are drawn or driven toward the base 12 to compress the mesh portion 44 between the first stem portion 46 and the second stem portion 48, each of which are generally non-compressible. In addition to being compressed, the mesh portion 44 expands outward from the longitudinal axis A (FIG. 5).

With reference to FIG. 6, the implant 10 can be compressed with a compression tool 90 if the fastener 60 is not included. The compression tool 90 generally includes a handle 92, and a shaft 94 including a distal end 96. A plurality of tool threads 98 are at the distal end 96. A flange 99 is positioned along the shaft 94 such that the flange 99 sits in the counterbore 26 of the implant 10 when the shaft 94 is inserted in the bore 42 of the implant 10, and the first few tool threads 98 closest to the distal end 96 cooperate with the bore threads 56 that are closest to the compressible mesh portion 44. To compress the mesh portion 44 and force the mesh portion 44 to expand from the longitudinal axis A, the compression tool 90 is rotated such that the tool threads 98 engage additional threads 56 of the bore 42, thereby drawing the second stem portion 48 toward the first stem portion 46 and compressing the mesh portion 44 therebetween.

With reference to FIG. 7 the implant 10 including the fastener 60 is implanted in a femur 102 to anchor the prosthetic femoral head 34. The implant 10 permits preservation of substantially all of femoral neck 104 and can be secured in the femur 102 without the need for other fastening mechanisms, such as transverse pins inserted through the neck 104 or bone cement. To implant the implant 10 in the femur 102, the natural head is resected and the femur 102 is milled or reamed through the neck 104. The stem 16 is inserted through the neck 104 such that the second surface 20 of the base 12 is seated on an anterior surface 106 of the neck 104.

To secure the implant 10 in the neck 104, the fastener 60 is rotated with the driver 80 to compress and expand the compressible mesh portion 44 as described above. The compressible mesh portion 44 expands from the longitudinal axis A to engage and extend into sidewalls 108 of the milled portion of the neck 104. While cooperation between the mesh portion 44 and the sidewalls 108 is typically sufficient to retain the implant in the femur 102, bone cement or other adhesives may be added to augment fixation. The femoral head 34 includes a female Morse taper 109, which cooperates with the male Morse taper connector 14 to secure the head 34 to the implant 10. If the implant 10 does not include the fastener 60, it is implanted in the same manner and the compression tool 90 can be used to compress and expand the mesh portion 44 as described herein. While the implant 10 is illustrated as a femoral implant, the compressible mesh portion 44 can be included in an anchoring stem of any other suitable type of implant to facilitate fixation of the implant to bone or tissue.

Figure 8A:
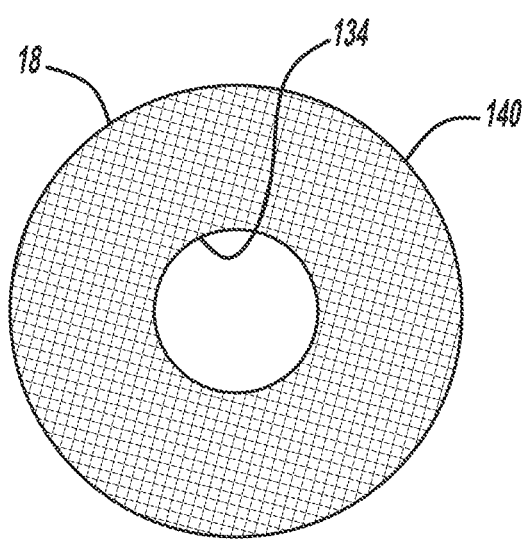
FIG. 8A is a cross-sectional view taken along line 8A-8A of FIG. 8.
Figure 8:
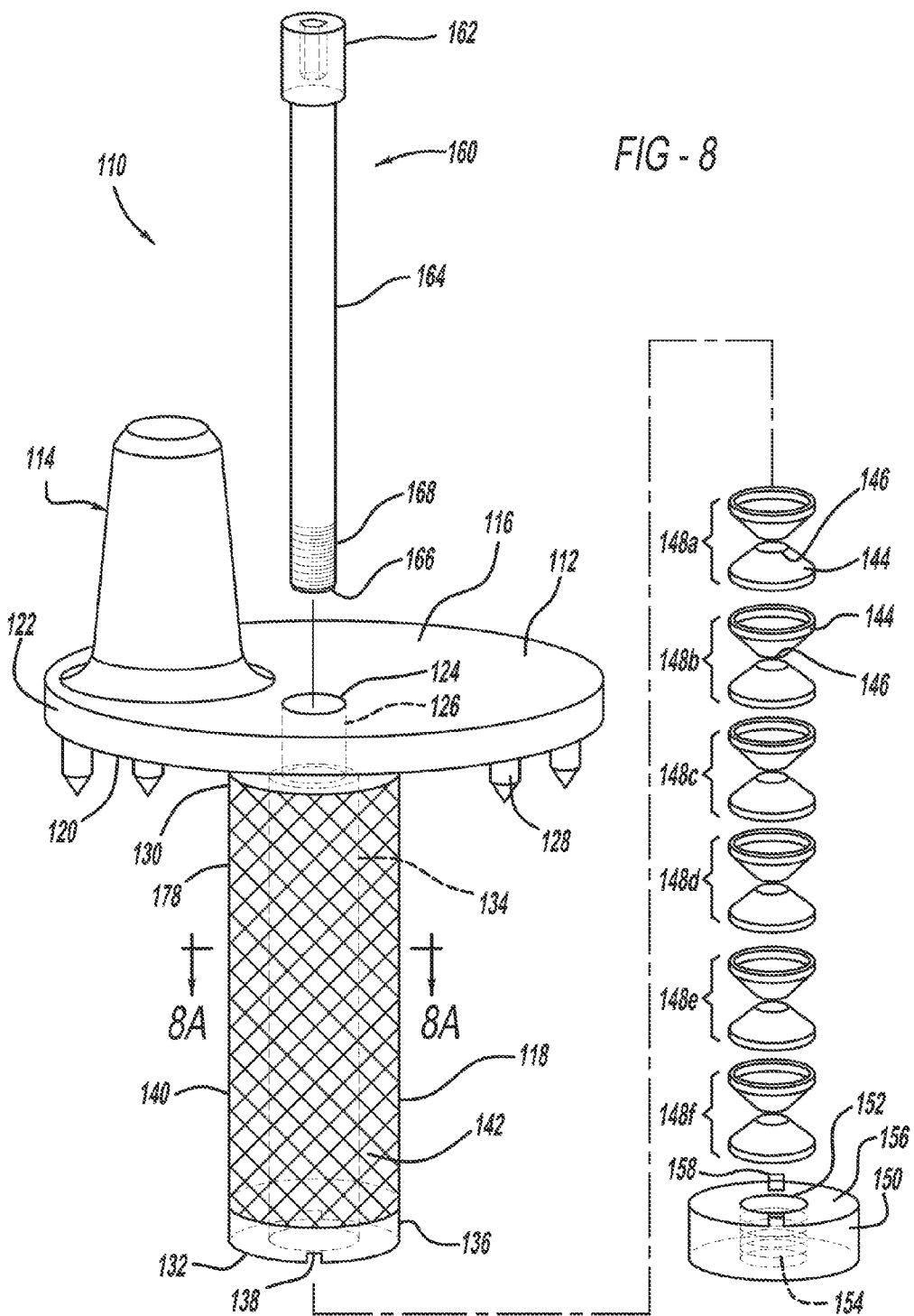
FIG. 8 is an exploded view of another implant according to the present teachings.

With additional reference to FIGS. 8-10, another implant according to the present teachings is illustrated at reference numeral 110. The implant 110 generally includes a base 112, a connector 114 mounted to a first surface 116 of the base 112, and an anchor or stem 118 mounted to a second surface 120 of the base 112. The first surface 116 is opposite to the second surface 120 and a side surface 122 extends therebetween. The connector 114 is substantially similar to the connector 14 of the implant 10, and thus the description of the connector 14 also describes the connector 114 of the implant 110.

The first and the second surfaces 116 and 120 are illustrated as planar, but can be curved. The first surface 116 defines an aperture 124 at generally an axial center thereof. Aligned with the aperture 124 is a counterbore 126, which is defined within the base 112. The aperture 124 and the counterbore 126 are aligned along a longitudinal axis B of the stem 118 (FIG. 9). Extending from the second surface 120 are a plurality of anti-rotational pins 128.

The stem 118 extends from the second surface 120 of the base 112. The stem 118 generally includes a base end 130 at the second surface 120 of the base 112 and a tip end 132 that is opposite to the base end 130. The base end 130 can be integral with the base 112 or secured thereto in any suitable manner, such as with a weld. The stem 118 defines a bore 134 that is aligned with the aperture 124 and the counterbore 126 along the longitudinal axis B. The bore 134 extends from the counterbore 126 to the tip end 132.

At the tip end 132 the stem 118 includes a solid portion 136. The solid portion 136 includes a pair of recesses 138 at the tip end 132. Between the solid portion 136 and the base 112 is a mesh portion 140, which defines a plurality of openings 142. The mesh portion 140 and the openings 142 are substantially similar to the mesh portion 44 and the openings 54 respectively of the implant 10. Thus, the above description of the mesh portion 44 and the openings 54 also describes the mesh portion 140 and the openings 142 respectively.

The bore 134 of the stem 118 is sized to house a plurality of washers 144. Each washer 144 generally defines a cone shape with an open tip 146. The washers 144 are arranged in multiple washer pairs, 148a-148f for example, such that the open tips 146 oppose one another. The washers 144 are configured to be compressible to apply a spring force that holds the implant in bone, as well as to potentially absorb forces applied to the base and act as dampers. The washers 144 are aligned in the bore 134 such that the open tips 146 are aligned along the longitudinal axis B (FIG. 9). In place of the washers 144 can be any suitable resilient component or compliant material.

The washers 144 are retained within the stem 118 with an end cap 150. The end cap 150 is generally annular and defines a receptacle 152 including cap threads 154. A proximal surface 156 of the end cap 150 includes tabs 158, which are sized to cooperate with the recesses 138 of the solid portion 136.

To retain the end cap 150 against the tip end 132 of the stem 118, a fastener 160 is used. The fastener 160 generally includes a head 162, a shaft 164 with a distal end 166, and fastener threads 168 at the distal end 166. The fastener 160 is inserted into the bore 134 such that the head 162 is seated in the counterbore 126 and abuts the nearest washer pair 148a. The shaft 164 extends through the open tips 146 of each of the washers 144, and into the receptacle 152 such that a few fastener threads 168 nearest the distal end 166 initially engage a few of the cap threads 154 nearest the proximal surface 156.

With reference to FIG. 10, to compress the mesh portion 140, thereby causing it to expand outward from the longitudinal axis B, the fastener 160 is rotated using any suitable device, such as the driver 80 illustrated in FIG. 4. Rotation of the fastener 160 causes the fastener threads 168 to engage additional cap threads 154 and extend through the receptacle 152 so that the fastener 160 extends through the end cap 150. Engagement between the head 162 of the fastener 160 and the counterbore 126 prevents the fastener 160 from moving along the longitudinal axis B, which results in the end cap 150 being pulled toward the base 112. As the end cap 150 is pulled toward the base 112, the mesh portion 140 is compressed between the end cap 150 and the base 112 along the longitudinal axis B.

With additional reference to FIG. 11, the implant 110 can be compressed with the compression tool 90 rather than the fastener 160. The compression tool 90 is initially positioned such that the flange 99 is seated in the counterbore 126 and the tool threads 98 only partially engage the cap threads 154. As the compression tool 90 is rotated, the tool threads 98 cooperate with and engage additional threads 154 of the end cap 150 to pull the end cap 150 toward the base 112. The mesh portion 140 is compressed between the end cap 150 and the base 112, thus causing the mesh portion 140 to expand outward from the longitudinal axis B. The compression tool 90 is rotated in an opposite direction to disengage the implant 110. The mesh portion 140 remains compressed after the compression tool 90 is removed due to cooperation with surrounding bone and properties of material included in the mesh portion 140.

Figure 12:
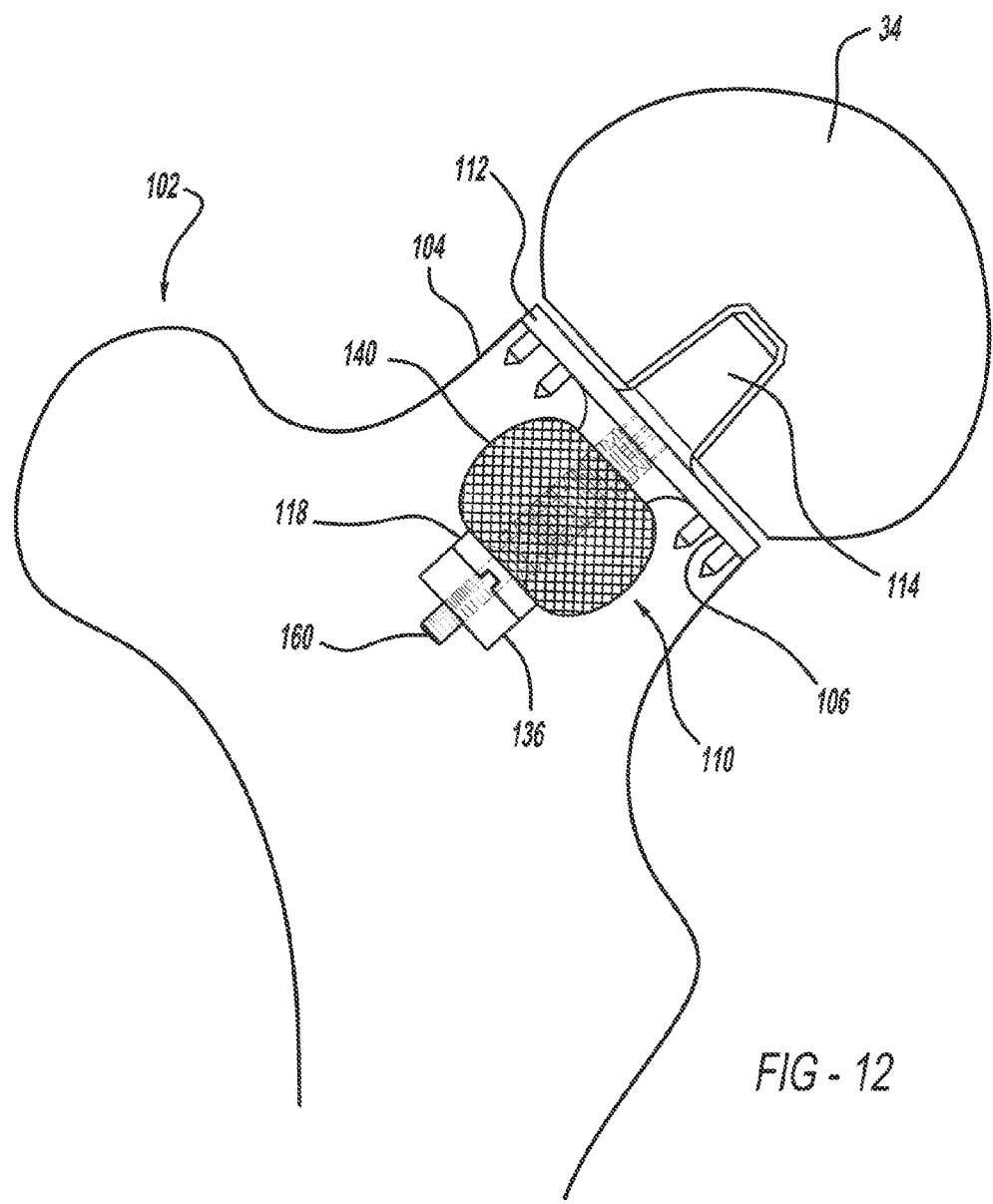
FIG. 12 illustrates the implant of FIG. 9 implanted in a femur.

With additional reference to FIG. 12, the implant 110 including the fastener 160 is implanted in the femur 102. The implant 110 is implanted in the femur 102 in substantially the same manner as the implant 10. Therefore, the above description of implantation of the implant 10 also applies to the implant 110. While the implant 110 is illustrated as a femoral implant, the mesh portion 140 can be included in an anchoring stem of any other suitable type of implant to facilitate fixation of the implant in bone or tissue.

Figure 13:
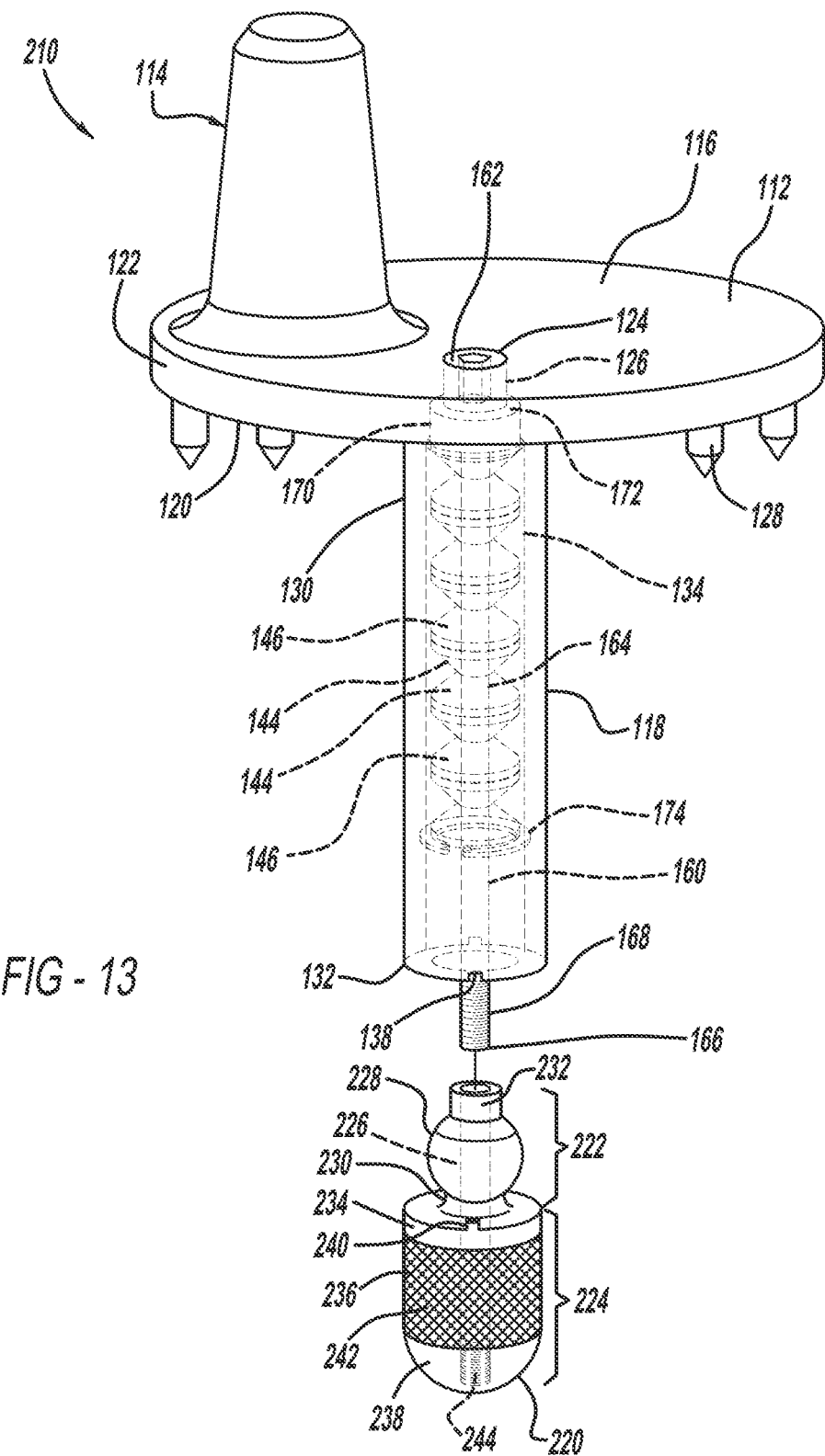
FIG. 13 is an exploded view of another implant according to the present teachings.

With reference to FIG. 13, another implant according to the present teachings is illustrated at reference numeral 210. The implant 210 includes various components that are substantially similar to components of the implant 110, and thus are illustrated with like reference numbers. For example, the implant 210 similarly includes the base 112, the connector 114, the anchor or stem 118, the washers 144 arranged in multiple washer pairs 148a-f in the stem, the aperture 124, the counterbore 126, and the bore 134.

The fastener 160 is positioned such that the head 162 is seated in the counterbore 126, the shaft 164 extends through the bore 134, and the distal end 166 extends beyond the tip end 132. The fastener 160 includes a flange 170 that abuts a shoulder 172 at a distal end of the counterbore 126 to prevent the fastener 160 from passing through the counterbore 126 and the base 112. To prevent the washers 144 from exiting the bore 134 at the tip end 132, a retention clip 174 is seated within the bore 134 distal to the most distal washer 144. The retention clip 174 can be secured within the bore 134 in any suitable manner. For example, the retention clip 174 can be seated within an annular recess defined within the bore 134.

Unlike the implant 110, the stem 118 of the implant 210 is solid and does not include the mesh portion 140. The stem 118 of the implant 210 can, however, include a mesh portion substantially similar to the mesh portion 140 as well.

The implant 210 further includes an expandable anchor cap 220. The anchor cap 220 generally includes an anchor head portion 222 and an anchor body portion 224. The anchor cap 220 defines a bore 226 that extends through the anchor head portion 222 and the anchor body portion 224. The bore 226 is aligned with a longitudinal axis C (FIG. 14) of the stem 118.

The head portion 222 generally includes a support sphere 228, which is connected to the anchor body portion 224 with a neck 230. At an end of the support sphere 228 opposite to the neck 230 is a boss 232. The anchor body portion 224 includes a solid base 234, a mesh portion 236, and a tip 238. Extending from the solid base 234 toward the neck 230 are tabs 240, which are sized and shaped to mate with the recesses 138 of the stem 118. The mesh portion 236 is similar to the mesh portion 44 of the implant 10 and the mesh portion 140 of the implant 110, and thus defines openings 242 that extend through the mesh portion 236 to the bore 226. The descriptions of the mesh portions 44 and 140 also describe the mesh portion 236. The tip 238 defines a concave outer shape and includes anchor threads 244 in the bore 226.

As illustrated in FIG. 14 for example, the anchor cap 220 is mounted spaced apart from the tip end 132 of the stem 118 with the fastener 160, or any other suitable fastening device. The fastener 160 is positioned such that the head 162 is seated in the counterbore 126 and the shaft 164 extends through the stem 118 and into the anchor cap 220. FIG. 15 is a cross-sectional view showing the fastener 160 extending through the mesh portion 236 of the anchor cap 220. The fastener threads 168 at the distal end 166 of the fastener 160 partially engage the anchor threads 244 of the anchor cap 220 at the tip portion 238 in the uncompressed position of FIG. 14.

With additional reference to FIG. 16, the mesh portion 236 of the anchor cap 220 is compressed by rotating the fastener 160 in any suitable manner, such as by using the driver 80 of FIG. 4. Rotation of the fastener 160 causes the fastener threads 168 to engage additional anchor threads 244 of the anchor cap 220 and draw the tip 238 toward the solid base 234, thereby compressing the mesh portion 236 therebetween and causing the mesh portion 236 to expand outward from the longitudinal axis C. The mesh portion 236 can be compressed before or after the anchor cap 220 is coupled to the anchor or stem 118, as further described herein.

With additional reference to FIG. 17, the mesh portion 236 of the anchor cap 220 can also be compressed with the compression tool 90. The compression tool 90 is orientated such that flange 99 is seated in the counterbore 126 and the shaft 94 extends through the stem 118 to engage the anchor cap 220. The shaft 94 extends through the anchor cap 220 such that the tool threads 98 cooperate with the anchor threads 244 at the tip 238 of the anchor cap 220. Rotation of the tool 90 causes the tool threads 98 to engage additional anchor threads 244 thereby pulling the anchor tip 238 toward the solid base 234 of the anchor cap 220 and compressing the mesh portion 236 therebetween. The compression tool 90 is rotated in an opposite direction to disengage the anchor cap 220. The mesh portion 236 remains compressed after the compression tool 90 is removed due to cooperation with surrounding bone and properties of material included in the mesh portion 236.

The implant 210 can be implanted in substantially the same manner as the implants 10 and 110. Thus the description of the implantation of the implants 10 and 110 also describes implantation of the implant 210. Unlike the implants 10 and 110, the anchor cap 220 includes the expandable mesh portion 236. Thus, once the implant 210 is seated in the femur 102, the fastener 160 is rotated to compress the mesh portion 236 thereby causing the mesh portion 236 to extend out from the longitudinal axis C and engage the surrounding bone of the femur 102 to secure the implant 210 to the femur 102. While the implant 210 is illustrated as a femoral implant, the anchor cap 220 including the compressible and expandable mesh portion 236 can be included in any other suitable type of implant to facilitate fixation of the implant in bone or tissue.

Figure 18:
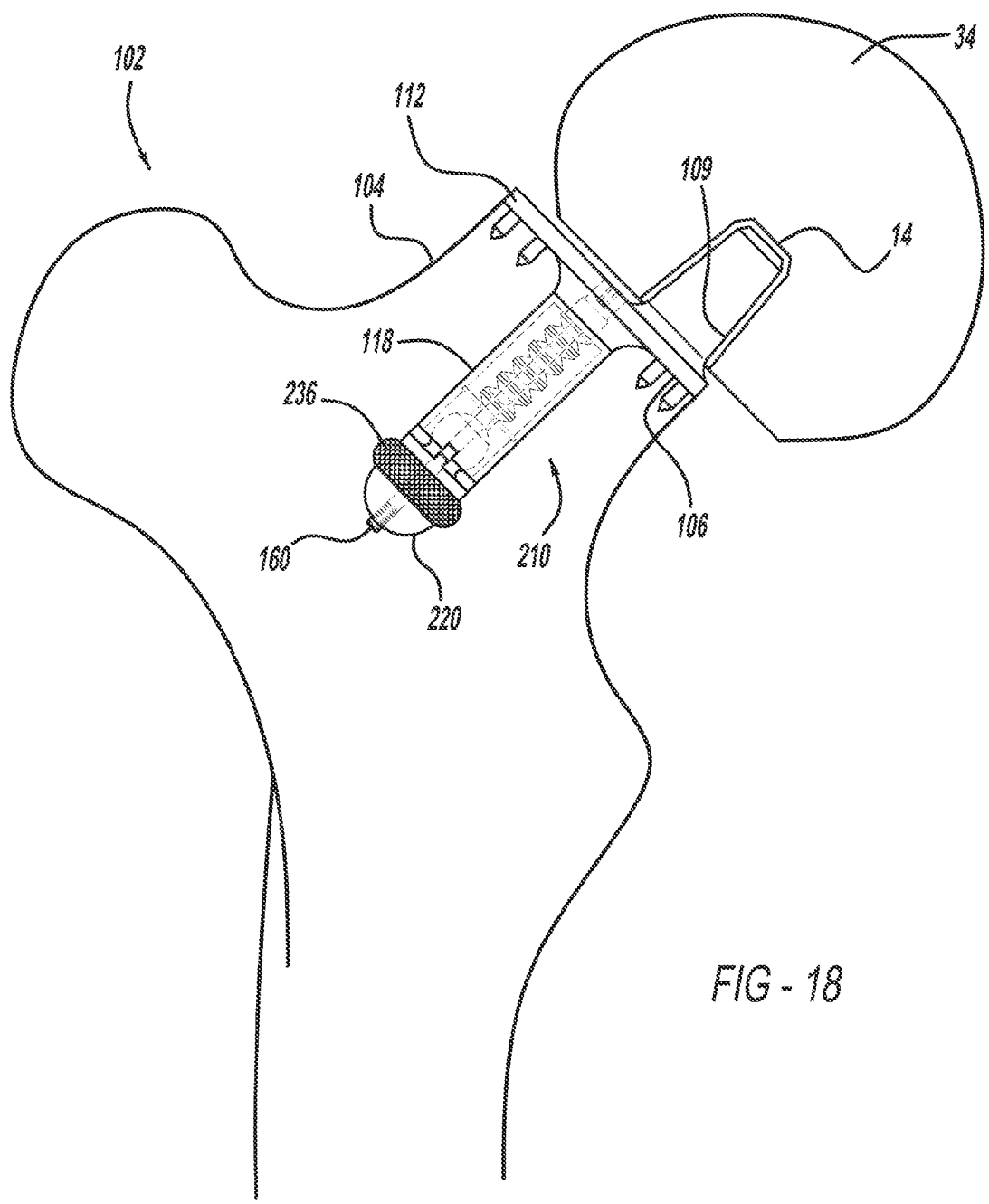
FIG. 18 illustrates the implant of FIG. 13 implanted in a femur.
Figure 18A:
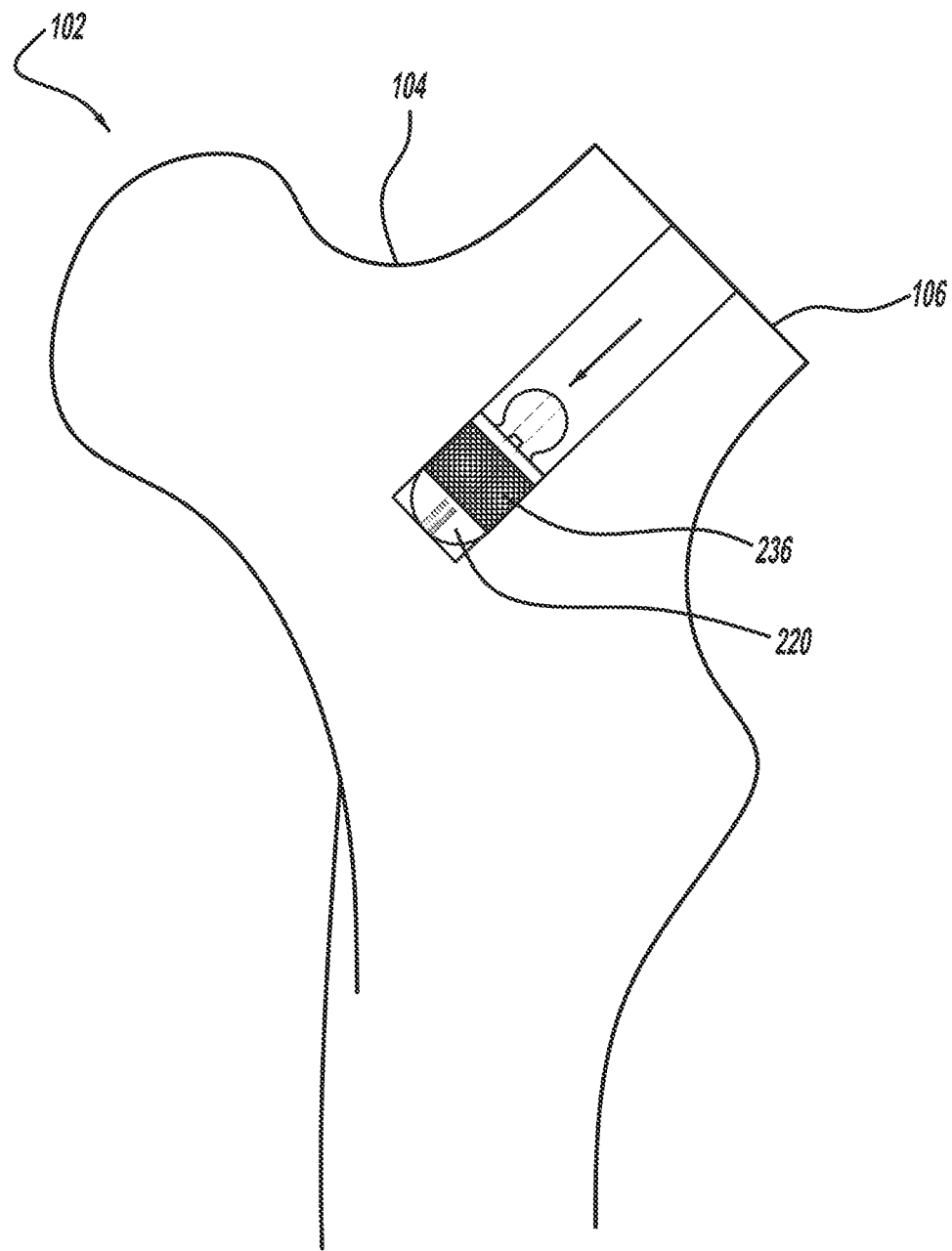
FIGS. 18A-18C illustrate implantation of the implant of FIG. 13 in the femur.
Figure 18B:
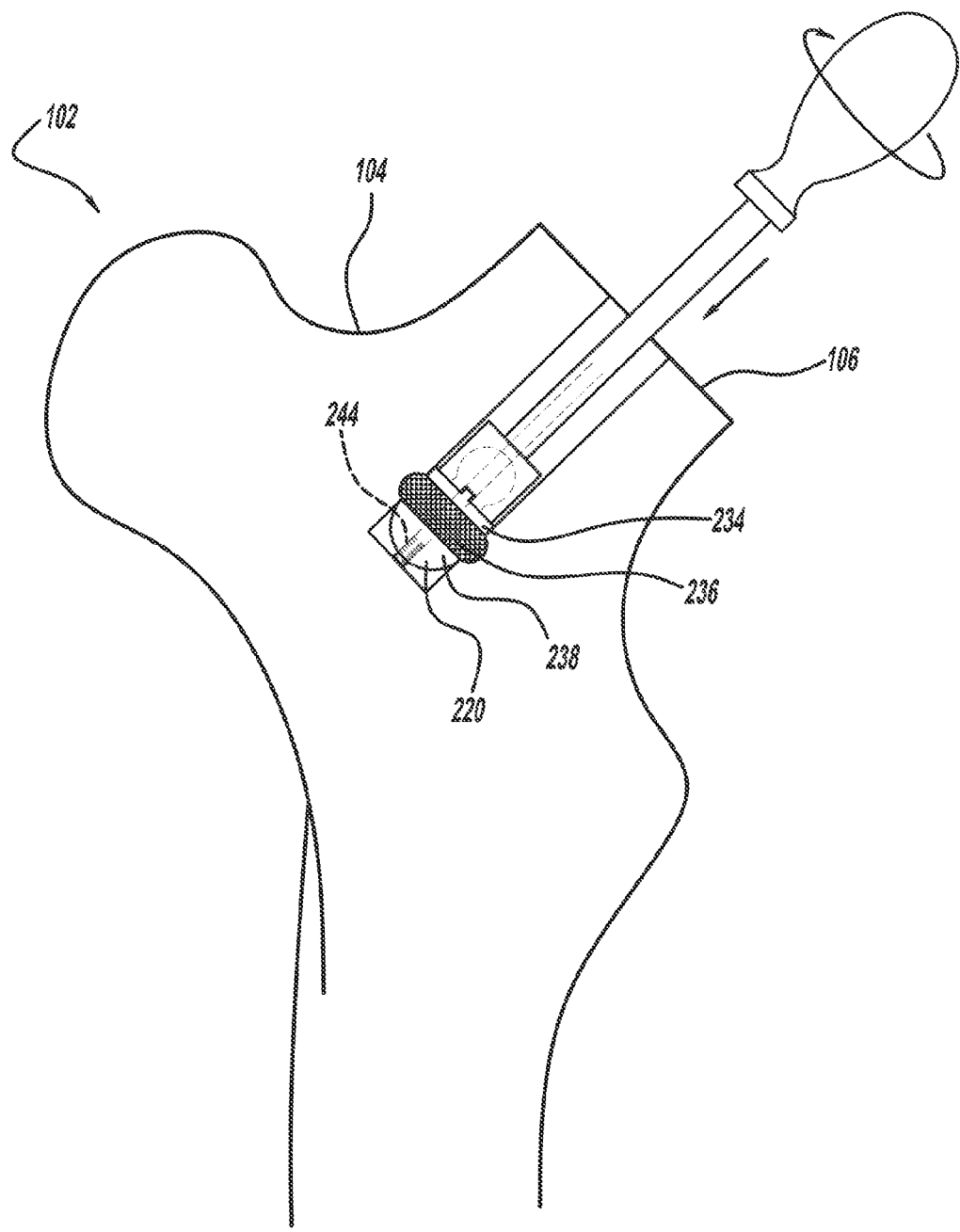
Figure 18C:
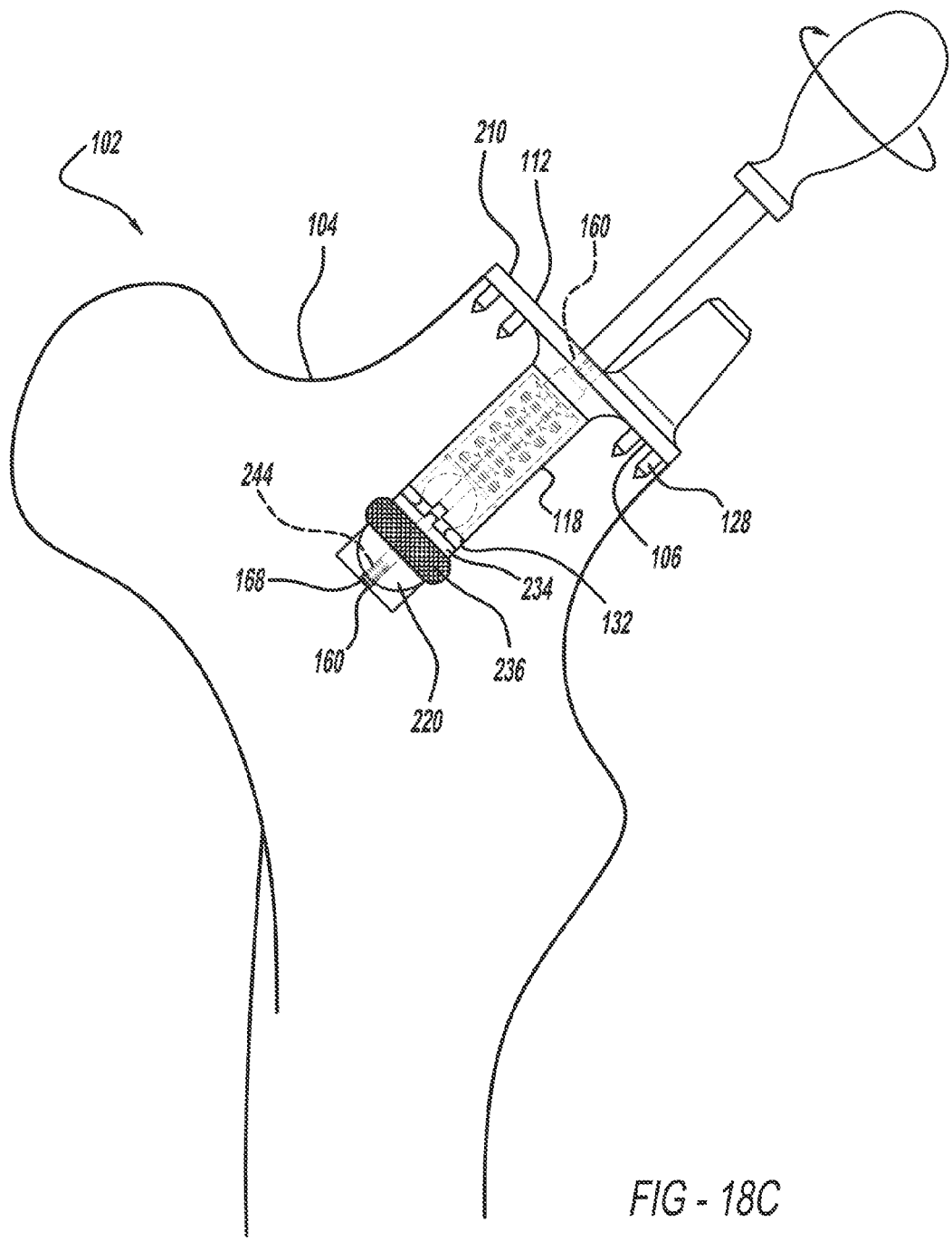

FIGS. 18A-18C illustrate an additional method for implanting the implant 210. With initial reference to FIG. 18A, the anchor cap 220 is initially implanted within any suitable bone hole in any suitable manner. For example, the anchor cap 220 can be implanted within a bone hole formed at the neck 104 of the femur 102. With additional reference to FIG. 18B, the mesh portion 236 is compressed such that it extends outward and into the bone hole to anchor the anchor cap 220 within the femur 102. The mesh portion 236 can be compressed in any suitable manner, such as with a tool that engages the anchor threads 244 and draws the tip 238 and the solid base 234 together.

As illustrated in FIG. 18C, the implanted anchor cap 220 serves as an anchor for the remainder of the implant 210. The stem 118 is inserted within the bone hole and the fastener 160 is threaded into engagement with the anchor threads 244. A gap is defined between the tip end 132 of the stem 118 and the solid base 234 of the anchor cap 220. The base 112 of the implant 110 is seated against the anterior surface 106 of the femur 102, and the pins 128 extending from the base 112 engage the anterior surface 106. As the fastener 160 is tightened, the fastener threads 168 of the fastener 160 thread further into the anchor threads 244 thereby drawing the remainder of the implant 210 toward the anchor cap 220, which compresses the base 112 against the femur 102, thereby facilitating healing and strengthening the femur bone 102.

An additional implant according to the present teachings is illustrated in FIGS. 19 and 20 at reference numeral 310. The implant 310 generally includes an anchor or sleeve 312 and a cap 314. The sleeve 312 generally includes a first end 316, a second end 318 that is opposite to the first end 316, and a sidewall 320 that extends between the first end 316 and the second end 318. The sidewall 320 is generally cylindrical, as illustrated in FIG. 20 for example. The sleeve 312 defines a bore 322 that extends through the sleeve 312 from the first end 316 to the second end 318. A longitudinal axis D of the sleeve 312 extends through an axial center of the bore 322.

The sleeve 312 includes a first sleeve portion 324 at the first end 316, a second sleeve portion 326 at the second end 318 and an intermediate portion 328 about half-way between the first end 316 and the second end 318. The first sleeve portion 324, the second sleeve portion 326, and the intermediate portion 328 are generally solid and generally not compressible. At the second end 318 the second sleeve portion 326 defines a recess 329.

Between the intermediate portion 328 and the first sleeve portion 324 is a first mesh portion 330. Between the intermediate portion 328 and the second sleeve portion 326 is a second mesh portion 332. Each of the first mesh portion 330 and the second mesh portion 332 define a plurality of openings 334. The first mesh portion 330 and the second mesh portion 332 are substantially similar to the compressible mesh portion 44 of the implant 10, the mesh portion 140 of the implant 110, and the mesh portion 236 of the anchor cap 220. Thus, the description of the mesh portions 44, 140, and 236 also describe the first and the second mesh portions 330 and 332 of the sleeve 312.

The cap 314 includes a first surface 336 and a second surface 338 that is opposite to the first surface 336. A side surface 340 extends between the first surface 336 and the second surface 338. The side surface 340 defines a generally cylindrical outer shape of the cap 314. The cap 314 defines a cap bore 342 therein. The cap bore 342 includes internal cap threads 344. A pair of flanges 346 extend from the first surface 336 and are sized and shaped to be received in the recess 329.

With additional reference to FIG. 21, a sleeve compression tool is illustrated at reference numeral 360. The tool 360 generally includes a handle 362, a shaft 364 that extends from the handle 362 and includes a distal end 366, and tool threads 368 at the distal end 366. Between the distal end 366 and the handle 362 is a flange 370. The sleeve compression tool 360 is operable to couple the sleeve 312 and the cap 314 together and compress the first and the second mesh portions 330 and 332, as described herein.

With additional reference to FIG. 22, the implant 310 is illustrated assembled and seated within an intramedullary canal 380 of the femur 102 at the isthmus 382 of the intramedullary canal 380. To implant the implant 310 in the intramedullary canal, the sleeve 312 is mated with the sleeve compression tool 360 such that flange 370 of the tool 360 mates with the first sleeve portion 324, the shaft 364 extends through the bore 322 to the second end 318 of the sleeve 312, and the tool threads 368 at the distal end 366 cooperate with the first few cap threads 344 of the cap 314 that are nearest the flange 346 in order to hold the cap 314 at the second end 318 of the sleeve 312.

As illustrated in FIG. 23 for example, with the implant 310 at the isthmus 382 of the intramedullary canal 380 the sleeve compression tool 360 is rotated so that the tool threads 368 engage additional cap threads 344 of the cap 314 and thus draw the cap 314 toward the first end 316 of the sleeve 312. As the cap 314 is drawn toward the first end 316, the sleeve 312 is compressed between the flange 370 and the cap 314. More specifically, the first mesh portion 330 and the second mesh portion 332 each compress along the longitudinal axis D and expand outward in a direction generally perpendicular to the longitudinal axis D. As the first mesh portion 330 and the second mesh portion 332 expand outward from the longitudinal axis D, the sidewall surfaces 320 thereof engage the intramedullary canal 380 to secure the implant 310 in position. After the first and second mesh portions 330 and 332 are compressed, the sleeve compression tool 360 is rotated in an opposite direction and removed. The intermediate portion 328 is solid and does not expand or compress, which helps maintain the bore 322 aligned with the longitudinal axis D and facilitates cooperation between the bore 322 and another implant, as described herein. The intermediate portion 328 can include a compressible and expandable mesh portion as well.

With additional reference to FIG. 24, the sleeve 312 is illustrated as anchoring a distal femoral implant 410. The distal femoral implant 410 is anchored to the sleeve 312 with a spindle 412 and a taper adaptor 414. The spindle 412 includes a spindle base 416 with an anchor or spindle stem 418 extending from a first side of the base 416 and a spindle male Morse taper surface connector 420 extending from a second side of the base 416, which is opposite to the first side. The spindle stem 418 includes spindle threads 422 at a distal end 424 thereof. The taper adaptor 414 includes a female Morse taper surface 426 and a male Morse taper surface 428, which are at opposite ends of the taper adaptor 414. The distal femoral implant 410 includes a female Morse taper surface 430 and an aperture 432 configured to receive a screw fastener 434.

To connect the spindle 412 to the sleeve 312, the spindle stem 418 is inserted through the bore 322 and the distal end 424 is threadably engaged with the cap threads 344 of the cap 314. The spindle 412 is orientated and the spindle stem 418 is provided with an appropriate length such that the spindle base 416 is at a distal end 103 of the femur 102 when coupled with the sleeve 312. The taper adaptor 414 is connected to the spindle 412 through cooperation between the female Morse taper surface 426 and the spindle male Morse taper surface connector 420. The distal femoral implant 410 is connected to the taper adaptor 414 through cooperation between the male Morse taper surface 428 and the female Morse taper surface 430 of the distal femoral implant 410. The fastener 434 can be used to further secure the distal femoral implant 410 to the taper adaptor 414. In addition to securing the distal femoral implant 410 to the femur 102, the sleeve 312 can be used to secure any suitable implant to any suitable bone or tissue.

With additional reference to FIG. 25, a body portion 440 of the taper adaptor 414 can include a mesh portion 442 that defines a plurality of openings 444. The mesh portion 442 is substantially similar to the mesh portions 44, 140, 236, 330, and 332 described herein, and thus the description of these mesh portions also describes the mesh portion 442. In response to a shock force across the assembly of FIG. 25, the mesh portion 442 compresses to absorb the shock and act as a damper. The mesh portion 442 thus increases patient comfort and reduces stress on the assembly of FIG. 25 to prolong the life of the assembly.

With additional reference to FIG. 26, the implant 10 of FIGS. 1-5 and 7 is illustrated with the base 12 including a mesh portion 480 between the first surface 18 of the base 12 and the second surface 20 of the base 12. The mesh portion 480 defines a plurality of openings 482 in the base 12. The mesh portion 480 is substantially similar to the mesh portions 44, 140, 236, 330, 332, 442 described herein, and thus the description of these mesh portions also describes the mesh portion 480. The mesh portion 480 is compressible to dampen shock forces experienced by the implant 10. The mesh portion 480 thus reduces stress on the implant 10 and the femoral head 34 connected thereto to prolong the life of the implant 10 and increase patient comfort.

With additional reference to FIG. 27A, another implant according to the present teachings is illustrated at reference numeral 510. The implant 510 generally defines a cup or hemispherical shape. The implant 510 includes a bone engaging surface 512 and an articulation surface 514 that is opposite to the bone engaging surface 512. The bone engaging surface 512 is generally convex in relation to the articulation surface 514. The articulation surface 514 is generally concave with respect to the bone engaging surface 512. The implant 510 is thus generally configured as an acetabular cup.

The articulation surface 514 defines a circular aperture 516 that provides an opening to a receptacle 518, which is also defined by the articulation surface 514. The articulation surface 514 further defines a threaded bore 520 at an axial center thereof. A longitudinal axis E extends through an axial center of the articulation surface 514, the aperture 516, and the threaded bore 520. Surrounding the aperture 516 is a planar base surface 522.

The implant 510 further includes a generally ring shaped mesh portion 530. The mesh portion 530 is proximate to both the planar base surface 522 and an equator of the implant 510. The mesh portion 530 defines openings 532 that extend entirely through the mesh portion 530. The mesh portion 530 is substantially similar to the mesh portions 44, 140, 236, 330, 332, 442, 480 described herein, and thus the description of these mesh portions also describes the mesh portion 530. As illustrated in FIG. 27B, the mesh portion 530 can be compressed along the longitudinal axis E. Such compression also causes expansion of the mesh portion 530 away from the longitudinal axis E in a direction that is generally perpendicular to the longitudinal axis E.

Figure 28:
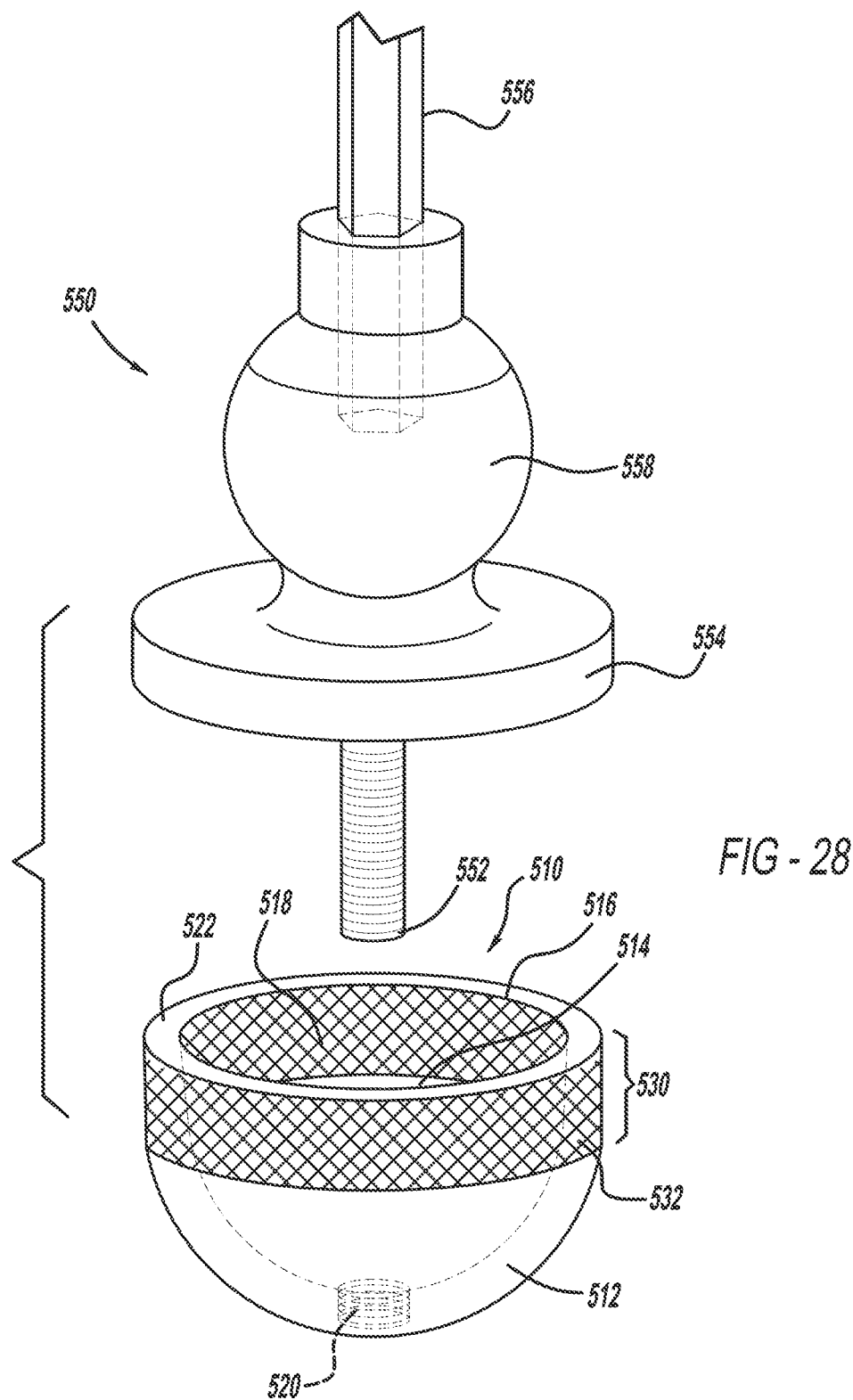
FIG. 28 is a perspective view of the implant of FIG. 27A and a cup compressor.

With additional reference to FIG. 28, the mesh portion 530 can be compressed using a suitable compression tool, such as the cup compressor 550. The cup compressor 550 generally includes a threaded tip 552, which extends from a flange 554. The flange 554 is connected to a handle 556 with a connector 558. To compress the mesh portion 530, the threaded tip 552 is inserted within the threaded bore 520 to bring the flange into contact with the planar base surface 522. The handle 556 is rotated so that the threaded tip 552 progressively threads into the threaded bore 520 and the flange 554 applies force to the planar base surface 522, thereby compressing the mesh portion 530. The handle 556 is rotated in an opposite direction to disengage the implant 510. The mesh portion 530 remains compressed after the cup compressor 550 is removed due to cooperation with surrounding bone and properties of material included in the mesh portion 530.

Figure 29:
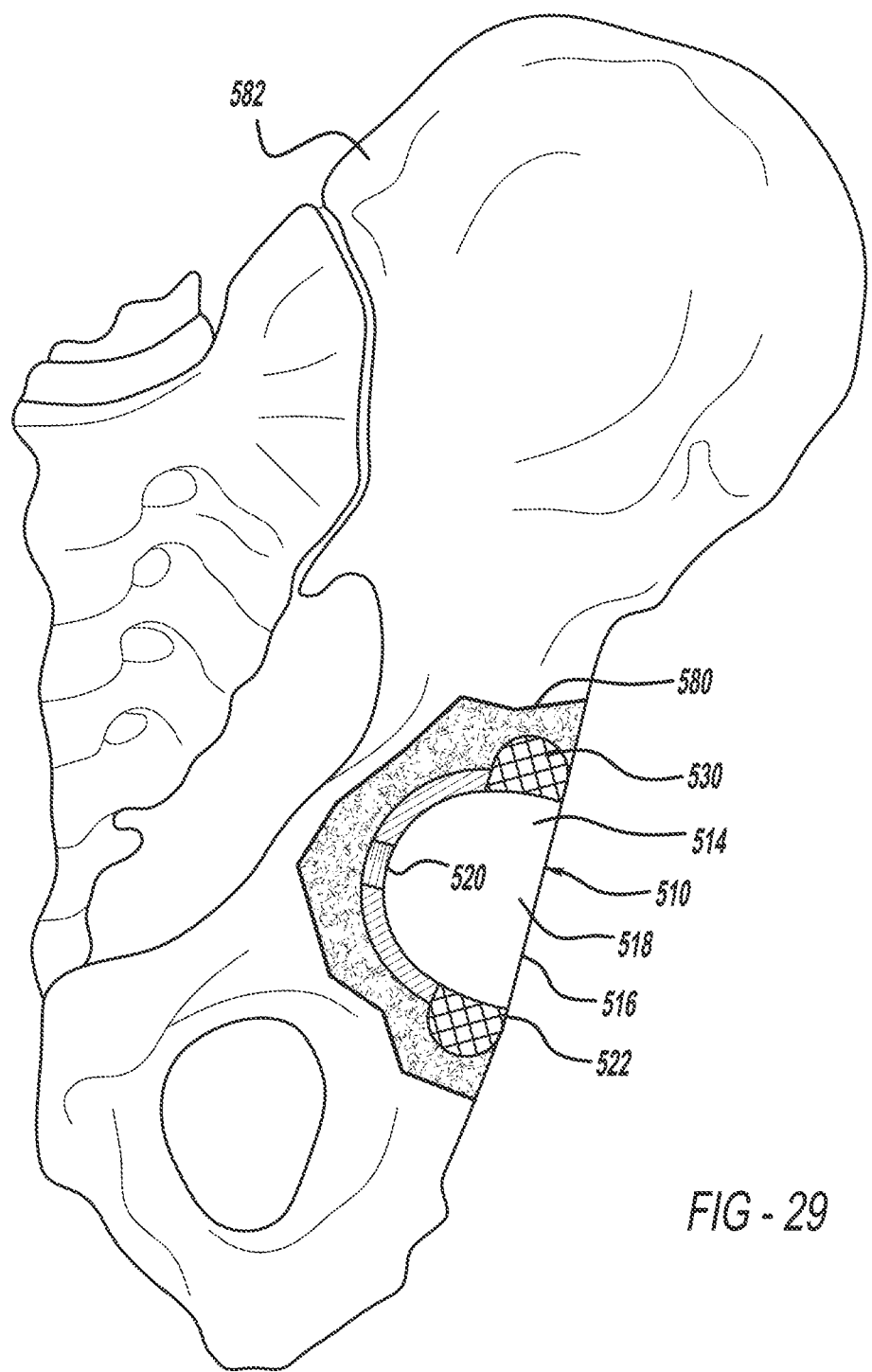
FIG. 29 illustrates the implant of FIG. 27A implanted in a pelvis.
Figure 35:
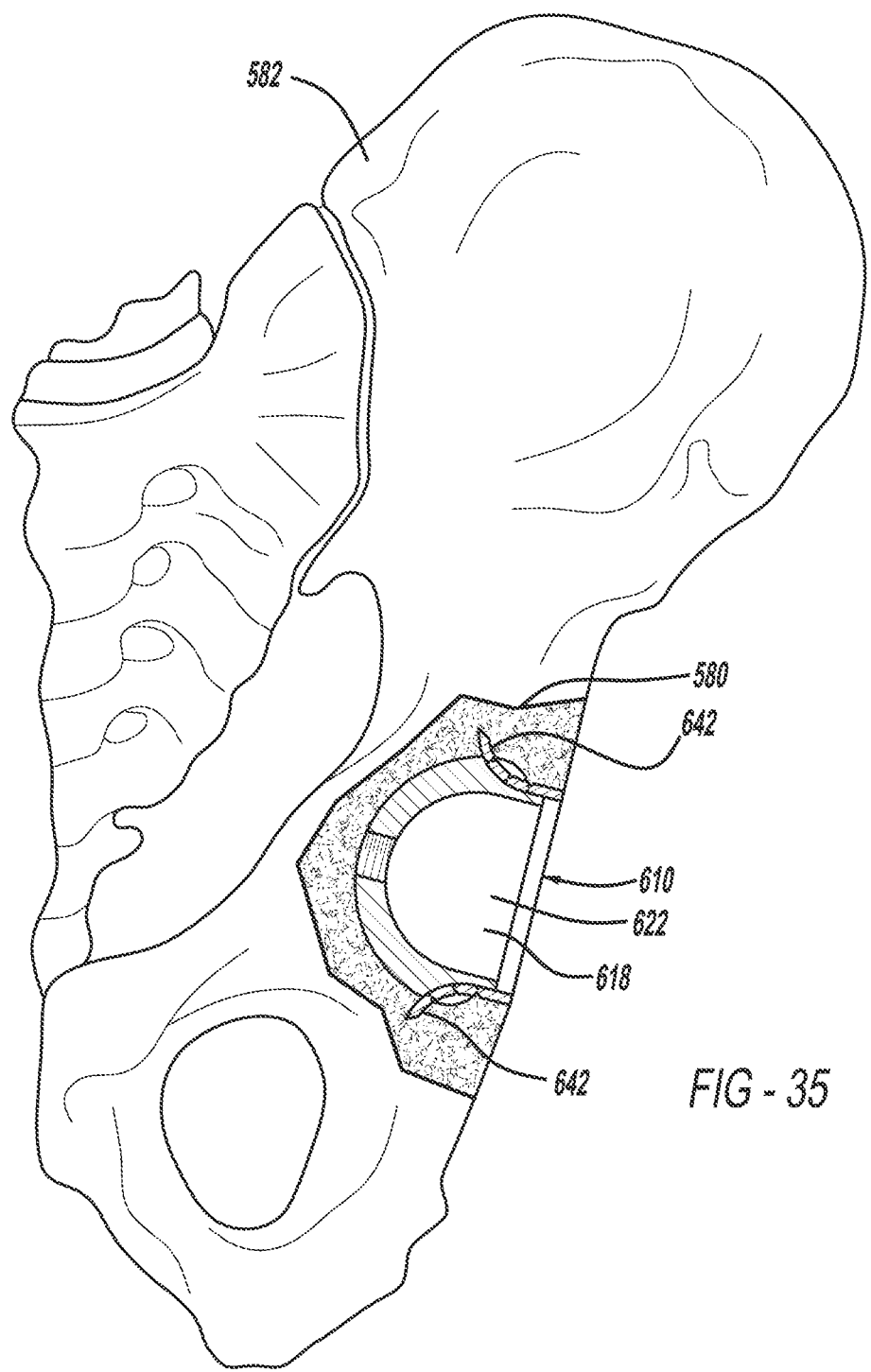
FIG. 35 illustrates the implant of FIG. 31 implanted in a pelvis.

With additional reference to FIG. 29, the implant 510 can be implanted into an acetabulum 580 of a pelvis 582, for example. The acetabulum 580 can be prepared in any suitable manner, such as by milling or reaming. To affix the implant 510 at the acetabulum 580, the implant 510 is mated with the cup compressor 550 as described above and then seated within the prepared acetabulum 580. Rotation of the handle 556 causes the threaded tip 552 to thread deeper within the threaded bore 520 and compress the flange 554 against the planar base surface 522, which thus compresses the mesh portion 530 along the longitudinal axis E. The mesh portion 530 also expands outward from the longitudinal axis E to engage the surrounding acetabulum 580 and secure the implant 510 therein. Securing the implant 510 with the mesh portion 530 can make anchor pins and screws unnecessary.

With additional reference to FIG. 30A, another implant according to the present teachings is illustrated at reference numeral 510'. The implant 510' is similar to the implant 510, and thus like features are designated with the same reference numbers, but include the prime (') symbol. The implant 510' further includes a flared or conical lip portion 534 of the bone engaging surface 512'. The flared portion 534 abuts the mesh portion 530', extends around the bone engaging surface 512' proximate to the equator of the implant 510', and extends outward from the longitudinal axis E. The mesh portion 530' extends along the longitudinal axis E from the flared portion 534. The flared portion 534 provides an enlarged base for the mesh portion 530', and thus the mesh portion 530' can have a larger outer diameter than the mesh portion 530, thereby allowing the mesh portion 530' to extend further into surrounding bone, for example, to enhance fixation of the implant 510' at an implant site. The implantation of the implant 510 described above also applies to the implant 510'.

FIG. 30B illustrates another implant according to the present teachings at reference numeral 510". The implant 510" is similar to the implant 510, and thus like features are designated with the same reference numbers, but include the double prime (") symbol. Unlike the implant 510, the mesh portion 530" and the planar base surface 522" attached thereto of the implant 510" are modular with respect to the remainder of the implant 510". The implant 510" includes a flange 536 and defines a seat 538 for the modular mesh portion 530". The mesh portion 530" is positioned over the flange 536 and positioned on the seat 538. Upon compression of the mesh portion 530", the mesh portion 530" expands into surrounding bone and retains the implant 510" at an implant site. The implant 510" can be compressed and implanted in a manner similar to that described above with respect to the implant 510, with the cup compressor 550 modified to accommodate the rigid flange 536.

With additional reference to FIGS. 31-35, another implant according to the present teachings is illustrated at reference numeral 610. The implant 610 generally includes a cup component 612 and a retention component 614. The cup component 612 generally defines a hemispherical shape. The cup component 612 includes a bone engaging surface 616 and an articulation surface 618 that is opposite to the bone engaging surface 616. The bone engaging surface 616 is generally convex in relation to the articulation surface 618. The articulation surface 618 is generally concave with respect to the bone engaging surface 616. The implant 610 is thus generally configured as an acetabular cup.

The articulation surface 618 defines a circular aperture 620 that provides an opening to a receptacle 622, which is also defined by the articulation surface 618. The articulation surface 618 further defines a threaded bore 624 at an axial center thereof. A longitudinal axis F extends through an axial center of the articulation surface 618 and the threaded bore 624. Surrounding the receptacle 622 is a planar base surface 625. At an exterior equator 626 of the cup component are a plurality of biasing surfaces 628, which are spaced apart about the equator. The biasing surfaces 628 are curved away from the longitudinal axis F.

The retention component 614 generally includes a retention ring 640 with a plurality of retention barbs 642. The retention barbs 642 protrude from an undersurface 644 of the retention ring 640 and are spaced apart about the retention ring 640. The retention barbs 642 include a pointed distal end 646 and a barb body 648 between the undersurface 644 of the retention ring 640 and the pointed distal end 646.

With reference to FIG. 33 for example, the barb body 648 includes an outer surface 650 and an inner surface 652. The outer surface 650 includes a plurality of outer notches 654 therein. The inner surface 652 includes a plurality of inner notches 656 therein. The outer notches 654 are larger than the inner notches 656 to facilitate bending of the retention barbs 642 away from the longitudinal axis F, as illustrated in FIG. 34. The retention component 614, including the retention barbs 642, can be made of any suitable type of material, such as a suitable metallic, fibrous, or polymeric component.

To assemble the implant 610, the retention barbs 642 are aligned with the biasing surfaces 628 and the retention component 614 is forced onto the cup component 612 with, for example, the cup compressor 550. In particular, the threaded tip 552 of the cup compressor 550 is connected to the threaded bore 624. As the threaded tip 552 is threaded deeper into the threaded bore 624, the flange 554 presses the retention ring 640 against the cup component 612 such that the undersurface 644 of the retention component 614 contacts the planar base surface 625 of the cup component 612 and the retention barbs 642 are forced into contact with the biasing surfaces 628, as illustrated in FIGS. 32 and 33 for example. Because the biasing surfaces 628 are curved outward from the longitudinal axis F, the retention barbs 642 are forced outward from the longitudinal axis F into an extended position, as illustrated in FIG. 34 for example. Movement of the retention barbs 642 to the extended position of FIG. 34 is facilitated by the outer notches 654 being larger than the inner notches 656, which results in less resistance to bending of the retention barbs 642 at the outer surface 650 thereof.

In the extended position of FIG. 34, the pointed distal ends 646 of each retention barb 642 extend into surrounding bone to secure the implant 610 at a desired implant site. For example and with reference to FIG. 35, the implant 610 can be implanted at an acetabulum 580 of a pelvis 582. After the acetabulum 580 is prepared, such as by reaming for example, the cup component 612 is seated in the acetabulum and the retention component 614 is compressed onto the cup component 612 using, for example, the cup compressor 550. Compression of the retention component 614 onto the cup component 612 causes the retention barbs 642 to extend into the surrounding bone, as described above, to secure the implant 610 at the acetabulum 580 without the need for bone cement.

Figure 36:
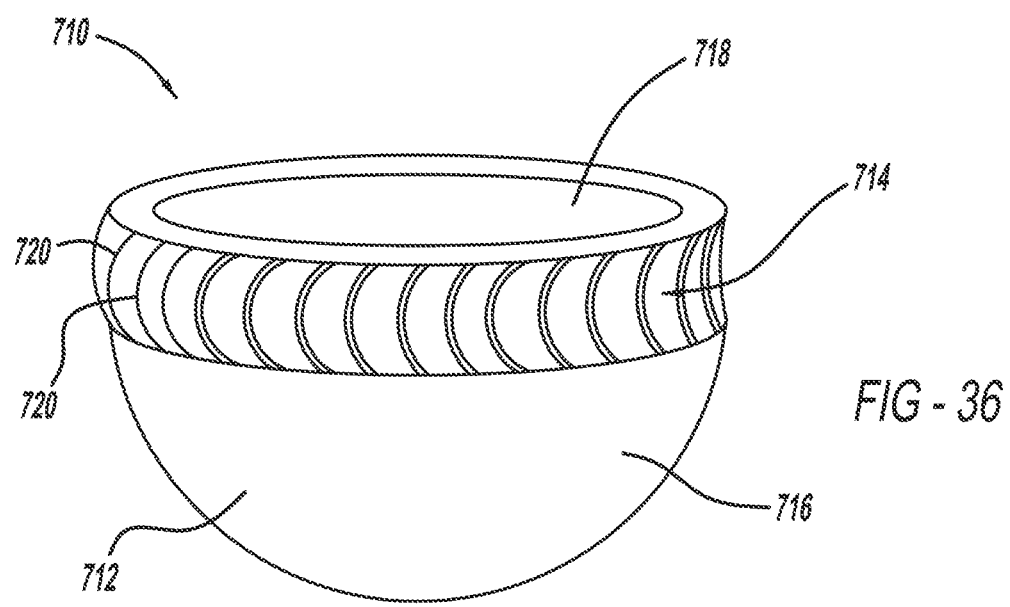
FIG. 36 is a side view of another implant according to the present teachings.
Figure 37:
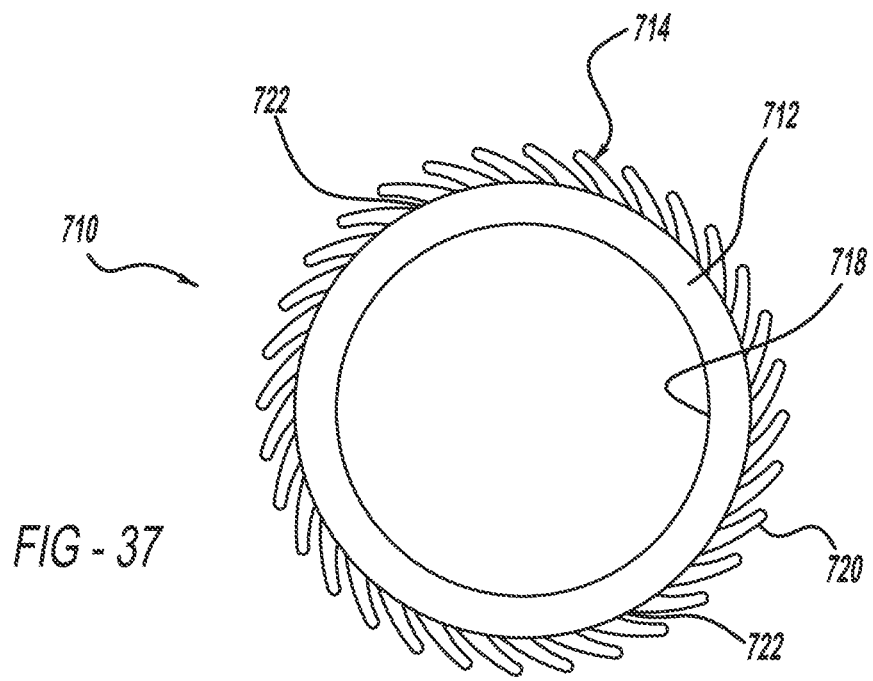
FIG. 37 is a top view of the implant of FIG. 36.

With additional reference to FIGS. 36 and 37, another implant according to the present teachings is illustrated at reference numeral 710. The implant 710 generally includes a cup component 712 and a retention component 714. The cup component 712 generally defines a hemispherical shape. The cup component 712 includes a bone engaging surface 716 and an articulation surface 718 that is opposite to the bone engaging surface 716. The bone engaging surface 716 is generally convex in relation to the articulation surface 718. The articulation surface 718 is generally concave with respect to the bone engaging surface 716. The implant 710 is thus generally configured as an acetabular cup.

The retention component 714 includes a plurality of retention fins 720 that extend outward from and extend around an outer perimeter wall 722 of the implant 710. The retention fins 720 can be made of any suitable material, including the material of the implant 710. For example, the fins 720 can be formed as a porous metal construct added to the bone engaging surface 716 through additive manufacturing. The porous metal construct can be similar to the Regenerex® porous metal construct sold by Biomet, Inc. and the additive manufacturing process can be similar to the electron beam melting process sold by Arcam, AB.

The retention fins 720 are generally flexible. The fins 720 can flex between an extended position, in which the fins 720 extend to a greatest extent outward from the outer wall of the implant 710, and a bent or engaged position, in which the fins 720 do not extend the greatest extent outward from the outer wall. In the extended position, which is illustrated in FIG. 37, the retention fins 720 are configured to engage bone to retain the implant 710 at an implantation site. During implantation, the implant 710 is impacted into bone. As the implant 710 is impacted, the retention fins 720 flex or bend inward to the bent or engaging position. The fins 720, however are biased and subsequently extend outward to engage surrounding bone after implantation to secure the implant 710 to the bone.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An acetabular cup implant comprising:
   a curved outer surface;
   a concave surface opposite to the curved outer surface, an axis of the acetabular cup implant extends through an axial center of the concave surface; and
   a retention component configured to compress along the axis and expand from the axis to engage surrounding bone or tissue at an implantation site to secure the implant at the implantation site.

2. The acetabular cup implant of claim 1, wherein the retention component includes a plurality of flexible fins that are configured to first compress during implantation into the implantation site and then expand into the surrounding bone at the implantation site.

3. The acetabular cup implant of claim 1, wherein a threaded bore is defined through the concave surface;
   wherein the threaded bore is configured to cooperate with a threaded tip of a compressor device including a flange; and
   wherein rotation of the threaded tip when the threaded tip is in cooperation with the threaded bore and the flange contacts an implant surface between the bone engaging outer surface and the concave surface, compresses the acetabular cup implant along the axis, compresses the retention component along the axis, and expands the retention component radially outward from the axis.

4. The acetabular cup implant of claim 3, wherein the acetabular cup implant includes at least one of a flared surface or a conical surface at the equator of the acetabular cup implant.

5. The acetabular cup implant of claim 1, wherein the concave surface is configured to cooperate with a femoral implant to replace a hip joint.

6. The acetabular cup implant of claim 1, wherein the retention component includes a compressible and expandable mesh aligned along the axis and defining a plurality of openings, the mesh is configured to compress along the axis and expand from the axis to engage surrounding tissue at the implantation site to secure the acetabular cup implant at the implantation site.

7. The acetabular cup implant of claim 6, wherein the mesh is included in an anchor and arranged between a first solid anchor portion and a second solid anchor portion.

8. The acetabular cup implant of claim 1, wherein the retention component is configured substantially at a rim of the acetabular cup implant.

9. An acetabular cup implant comprising:
   a curved bone engaging outer surface;
   a concave surface opposite to the bone engaging surface, an axis of the acetabular cup implant extending through an axial center of the concave surface; and
   a retention component including a retention ring, wherein upon compression, the retention component is forced outward from the axis to engage surrounding bone or tissue at an implantation site to secure the acetabular cup implant at the implantation site.

10. The acetabular cup implant of claim 9, further comprising a threaded bore at the axis.

11. The acetabular cup implant of claim 10, wherein the threaded bore is configured to cooperate with a threaded tip of a compressor device including a flange; and
    wherein rotation of the threaded tip when the threaded tip is in cooperation with the threaded bore compresses the retention ring against the cup component.

12. The acetabular cup implant of claim 9, further comprising a plurality of concave biasing surfaces spaced apart about an equator of the curved bone engaging surface;
    wherein the retention component includes a plurality of retention barbs extending from the retention ring and spaced apart about the retention ring; and
    wherein upon compression of the retention component, the retention barbs contact the biasing surfaces and the retention barbs are forced outward from the axis to engage surrounding bone or tissue at an implantation site to secure the acetabular cup implant at the implantation site.

13. The acetabular cup implant of claim 12, wherein the biasing surfaces and the retention barbs are spaced apart at similar intervals.

14. The acetabular cup implant of claim 12, wherein each barb includes an outer surface and an inner surface that is opposite to the outer surface; and
    wherein the outer surface defines at least one first notch therein and the inner surface defines at least one second notch therein, the first notch is larger than the second notch.

15. The acetabular cup implant of claim 9, wherein the retention component includes a compressible and expandable mesh aligned along the axis and defining a plurality of openings, the mesh configured to compress along the axis and expand from the axis to engage surrounding tissue at the implantation site to secure the acetabular cup implant at the implantation site.

16. An acetabular cup implant comprising:
an outer surface;
a concave surface opposite to the outer surface;
a centerline axis extending through an axial center of the concave surface; and
a retention component configured to compress along the centerline axis and expand from the centerline axis to engage surrounding bone or tissue at an implantation site to secure the acetabular cup implant at the implantation site.

17. The acetabular cup implant of claim 16, further comprising:
a threaded bore defined through the concave surface;
wherein the threaded bore is configured to cooperate with a threaded tip of a compressor device including a flange; and
wherein rotation of the threaded tip when the threaded tip is in cooperation with the threaded bore and the flange is in contact with an implant surface between the bone engaging outer surface and the concave surface, compresses the acetabular cup implant along the centerline axis, compresses the retention component along the centerline axis, and expands the retention component radially outward from the centerline axis.

18. The acetabular cup implant of claim 16, wherein the acetabular cup implant includes at least one of a flared surface or a conical surface at an equator of the implant.

19. The acetabular cup implant of claim 16, wherein the retention component includes a compressible and expandable mesh aligned along the centerline axis and defining a plurality of openings, the mesh configured to compress along the centerline axis and expand from the centerline axis to engage surrounding tissue at the implantation site to secure the acetabular cup implant at the implantation site.

20. The acetabular cup implant of claim 16, further comprising a plurality of concave biasing surfaces spaced apart about an equator of the outer surface;
wherein the retention component includes a plurality of retention barbs extending from and spaced apart about the retention component; and
wherein upon compression of the retention component, the retention barbs contact the biasing surfaces and the retention barbs are forced outward from the axis to engage surrounding bone or tissue at an implantation site to secure the acetabular cup implant at the implantation site.

* * * * *

UNITED STATES PATENT AND TRADEMARK OFFICE
CERTIFICATE OF CORRECTION

PATENT NO. : 9,744,047 B2
APPLICATION NO. : 14/635056
DATED : August 29, 2017
INVENTOR(S) : Meridew et al.

Page 1 of 1

It is certified that error appears in the above-identified patent and that said Letters Patent is hereby corrected as shown below:

On the Title Page

In item (65), in "Prior Publication Data", in Column 1, Line 1, after "2015", insert --¶US 2017/0189189 A9 Jul. 6, 2017--

Signed and Sealed this
Eleventh Day of June, 2019

Andrei Iancu
*Director of the United States Patent and Trademark Office*